(12) United States Patent
Dumont et al.

(10) Patent No.: US 11,434,755 B2
(45) Date of Patent: Sep. 6, 2022

(54) DETERMINING ASPHALTENE ONSET

(71) Applicant: Schlumberger Technology Corporation, Sugar Land, TX (US)

(72) Inventors: Hadrien Dumont, Paris (FR); Thomas Pfeiffer, Katy, TX (US); Vinay K. Mishra, Katy, TX (US); German Garcia, Katy, TX (US); Christopher Harrison, Auburndale, MA (US); Oliver Mullins, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 16/170,149

(22) Filed: Oct. 25, 2018

(65) Prior Publication Data

US 2019/0128117 A1 May 2, 2019

Related U.S. Application Data

(60) Provisional application No. 62/577,915, filed on Oct. 27, 2017.

(51) Int. Cl.
*E21B 49/08* (2006.01)
*G01N 33/28* (2006.01)
*E21B 49/10* (2006.01)

(52) U.S. Cl.
CPC ............ *E21B 49/08* (2013.01); *E21B 49/081* (2013.01); *E21B 49/10* (2013.01); *G01N 33/2823* (2013.01); *E21B 49/0875* (2020.05)

(58) Field of Classification Search
CPC ........ E21B 49/08; E21B 49/081; E21B 49/10; E21B 49/0875; E21B 49/0813; E21B 49/0815; E21B 49/083; E21B 49/087; G01N 33/2823; G01N 33/2835; G01N 29/00; G01N 29/02; G01N 29/024–036; G01N 29/227; G01N 9/00; G01N 9/002; G01N 2291/028; G01N 2291/02872; G01N 2291/02881
See application file for complete search history.

(56) References Cited

U.S. PATENT DOCUMENTS

| | | | |
|---|---|---|---|
| 6,880,402 B1 * | 4/2005 | Couet | B08B 3/12 73/579 |
| 9,303,510 B2 | 4/2016 | Dumont et al. | |
| 2007/0227241 A1 * | 10/2007 | DiFoggio | G01N 29/024 73/152.23 |
| 2014/0238667 A1 * | 8/2014 | Dumont | E21B 49/082 166/250.01 |
| 2015/0159484 A1 * | 6/2015 | Dumont | E21B 49/088 166/250.02 |
| 2015/0211357 A1 * | 7/2015 | Chen | E21B 47/06 73/152.27 |

(Continued)

*Primary Examiner* — George S Gray
(74) *Attorney, Agent, or Firm* — Trevor G. Grove

(57) ABSTRACT

Methods and downhole tools for operation within in a wellbore that extends into a subterranean formation. The operation includes simultaneously causing a change in a first parameter of fluid drawn into the downhole tool from the formation and determining a change in a second parameter of the fluid relative to the change in the first parameter. A third parameter of the fluid is determined based on the first and second parameter changes.

20 Claims, 13 Drawing Sheets

(56) References Cited

U.S. PATENT DOCUMENTS

2016/0208601 A1\* 7/2016 Molla ................ G01N 33/2811
2017/0175524 A1   6/2017 Dumont et al.
2017/0284197 A1\* 10/2017 Dumont ................ E21B 47/07
2017/0328202 A1  11/2017 Hsu et al.
2017/0342828 A1  11/2017 Dumont et al.

\* cited by examiner

DETERMINING ASPHALTENE ONSET

CROSS-REFERENCE TO RELATED APPLICATIONS

This application claims priority to and the benefit of U.S. Provisional Application No. 62/577,915, titled "Determining Asphaltene Onset Point/Pressure," filed Oct. 27, 2017, the entire disclosure of which is hereby incorporated herein by reference.

BACKGROUND OF THE DISCLOSURE

Wellbores are drilled to penetrate subterranean formations for hydrocarbon prospecting and production. During drilling operations, evaluations of the subterranean formation may be performed to locate hydrocarbon-producing formations, and/or to manage the production of hydrocarbons from these formations. To conduct formation evaluations, a drillstring may include one or more drilling tools that test and/or sample the surrounding formation, or a wireline tool may be deployed (after removing the drillstring) into the wellbore to test and/or sample the formation. These drilling tools and wireline tools, as well as other wellbore tools conveyed on coiled tubing, drill pipe, casing, and other conveyance means, are also referred to herein as "downhole tools."

Formation evaluation may involve drawing fluid from the formation into a downhole tool for testing and/or sampling. One or more probes, packers, and/or other devices may be extended from the downhole tool to isolate a region of the wellbore wall and thereby establish fluid communication with the subterranean formation surrounding the wellbore. Fluid may then be drawn into the downhole tool through the isolated wellbore wall region. Within the downhole tool, the fluid may be directed to one or more fluid analyzers and/or other sensors employed to detect properties of the fluid, including while the downhole tool remains within the wellbore.

SUMMARY OF THE DISCLOSURE

This summary is provided to introduce a selection of concepts that are further described below in the detailed description. This summary is not intended to identify indispensable features of claimed subject matter, nor is it intended for use as an aid in limiting the scope of claimed subject matter.

The present disclosure introduces a method including obtaining a sample of fluid from a subterranean formation, and then reducing a first parameter of the sample while measuring a second parameter of the sample. The first parameter is pressure or temperature. The method also includes determining asphaltene onset point of the sample based on the second parameter measurements.

The present disclosure also introduces a method including operating a downhole tool within in a wellbore that extends into a subterranean formation. The operation includes simultaneously causing a change in a first parameter of fluid drawn into the downhole tool from the formation and determining a change in a second parameter of the fluid relative to the change in the first parameter. The method also includes determining a third parameter of the fluid based on the first and second parameter changes.

The present disclosure also introduces a method including assessing an accuracy of a previously determined value of a phase-change parameter of a fluid drawn into a downhole tool from a subterranean formation. The accuracy assessment includes determining, at each of multiple different wavelengths, a difference between a maximum measured optical density of the fluid and another measured optical density of the fluid that corresponds to the previously determined value of the phase-change parameter. The method also includes determining whether the determined differences increase monotonically relative to decreasing values of the wavelengths.

These and additional aspects of the present disclosure are set forth in the description that follows, and/or may be learned by a person having ordinary skill in the art by reading the material herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
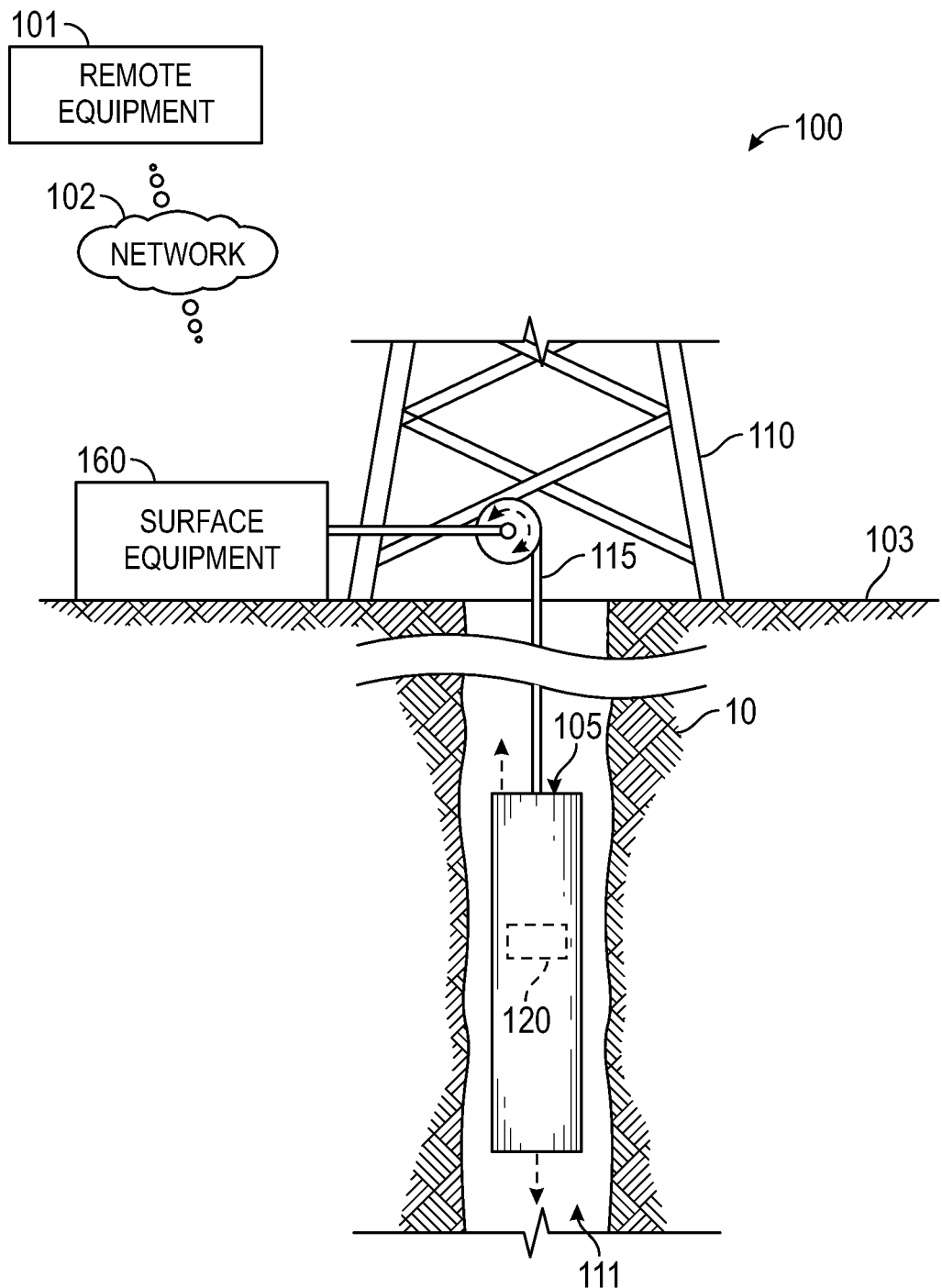
FIG. 1 is a schematic view of at least a portion of an example implementation of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed.

Moreover, while a formation is technically a fundamental unit of lithostratigraphy, namely a subterranean body that is so distinctive and continuous that it can be mapped (i.e., a body of rock and/or other strata of predominantly one type or a combination of types), and a reservoir is technically a subterranean body of strata having sufficient porosity and permeability to store and transmit fluids, the terms "formation" and "reservoir" may be used interchangeably within the scope of the present disclosure.

Asphaltene onset pressure and asphaltene onset point may also be collectively referred to as AOP within the scope of the present disclosure. However, a person having ordinary skill in the art will recognize that some occurrences of AOP may refer to just asphaltene onset pressure and not asphaltene onset point, while other occurrences of AOP may refer to just asphaltene onset point and not asphaltene onset pressure.

The present disclosure is related to determination of AOP, or multiple AOPs, and perhaps one or more saturation points of reservoir fluids downhole. The present disclosure is also related to a fluid instability indicator based on downhole fluorescence measurements, perhaps with one or more independent sensors in addition to optical spectrometers. Coupled with optical density (OD), gas/oil ratio (GOR) measurements, and perhaps other parameters, the present disclosure introduces one or more aspects related to determining AOP and saturation points of reservoir fluids downhole. Fluorescence measurements may be utilized with measurements from downhole micro-PVT (pressure, volume, temperature) cells, modular and/or other sample chambers, modular and/or other sample bottles, and/or other data acquisition means to determine AOP apart from optical measurements. Example implementations disclosed herein may be with regard to downhole tool retraction. Other downhole measured fluid properties, such as density, viscosity, nuclear magnetic resonance (NMR), compressibility, formation volume factor, speed of sound, resistivity, interfacial tension, dielectric constant, refractive index, and/or others, may also be utilized according to one or more aspects of the present disclosure to determine AOP, wax appearance temperature (WAT), saturation points, and/or other parameters/answer products.

One or more aspects of the present disclosure may also or instead relate to a phase change measured or observed by downhole fluid analysis (DFA) methods, including (1) fluid to fluid-solid (AOP); (2) fluid to fluid-solid (WAT); (3) liquid to liquid-gas (saturation pressure (PSat) or bubble point (Pb)); and/or (4) gas to gas-liquid (PSat or dew point (Pd)).

The present disclosure also introduces determining AOP, Pb, and/or Pd downhole in real-time, such as by operating a pump of the downhole tool to reduce captured formation fluid pressure, instead of (or in addition to) while retrieving the downhole tool to surface.

FIG. 1 is a schematic view of an example system 100 that may be employed onshore and/or offshore according to one or more aspects of the present disclosure, representing an example environment in which one or more aspects described above (and below) may be implemented, such as to perform one or more aspects of the methods described herein and/or otherwise within the scope of the present disclosure. As depicted in FIG. 1, a downhole tool 105 may be suspended from a platform, rig, derrick, and/or other wellsite structure 110 in a wellbore 111 formed in one or more subterranean reservoirs 10. The downhole tool 105 may be or comprise one or more tools, one or more of which may be or comprise an acoustic tool, a conveyance tool, a density tool, a DFA tool, an electromagnetic (EM) tool, a reservoir evaluation tool (also known in the art as a formation evaluation tool), a magnetic resonance tool, a monitoring tool, a neutron tool, a nuclear tool, a photoelectric factor tool, a porosity tool, a reservoir characterization tool, a resistivity tool, a sampling tool, a seismic tool, a surveying tool, and/or a telemetry tool, although other downhole tools are also within the scope of the present disclosure.

The downhole tool 105 may be deployed from the wellsite structure 110 into the wellbore 111 via a conveyance means 115, which may be or comprise a wireline cable, a slickline cable, and/or coiled tubing, although other means for conveying the downhole tool 105 within the wellbore 111 are also within the scope of the present disclosure. As the downhole tool 105 operates, outputs of various numbers and/or types from the downhole tool 105 and/or components thereof (one of which is designated by reference number 120) may be sent via the conveyance means 115 and/or otherwise to a logging and control system and/or other surface equipment 160 at the wellsite surface 103, and/or may be stored in various numbers and/or types of memory for subsequent recall and/or processing after the downhole tool 105 is retrieved to surface 103. Such data may also be transmitted from the surface equipment 160 to remote equipment 101 disposed remote from the system 100, perhaps hundreds or thousands of kilometers away. For example, such transmission may be via one or more networks 102, such as may include one or more of a cellular network, a satellite network, a wide area network, a local area network, and/or other types of networks, including wired and/or wireless networks.

Figure 2:
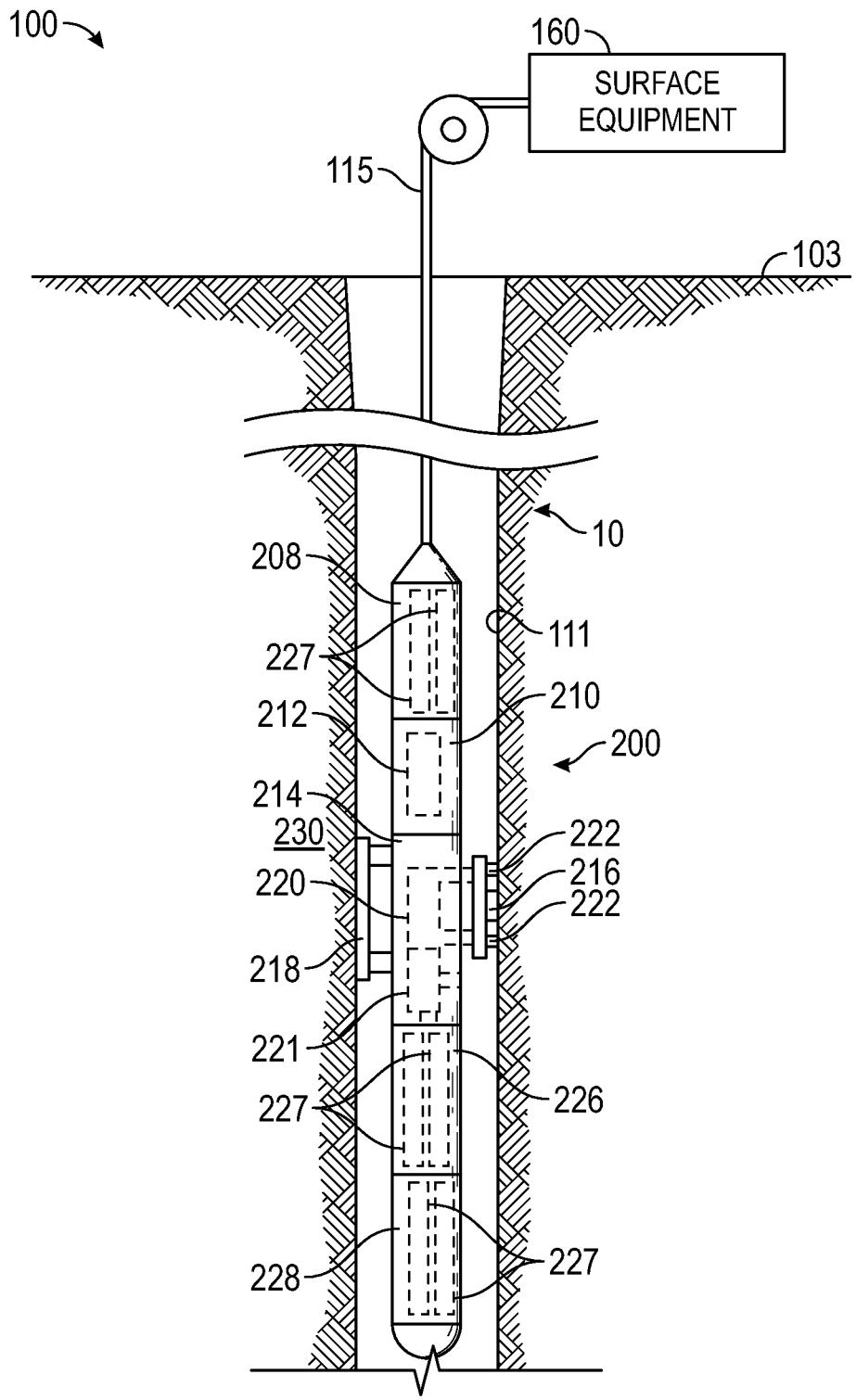
FIG. 2 is a schematic view of at least a portion of an example implementation of apparatus according to one or more aspects of the present disclosure.

FIG. 2 is a schematic view of an example implementation of the system 100 shown in FIG. 1, including an example implementation of the downhole tool 105 shown in FIG. 1 and designated in FIG. 2 by reference number 200. The downhole tool 200 is operable to engage a portion of a sidewall of the wellbore 111 penetrating the reservoir 10. The downhole tool 200 may be utilized to perform one or more aspects of the methods described herein and/or otherwise within the scope of the present disclosure.

The downhole tool 200 is suspended in the wellbore 111 from a lower end of the conveyance means 115. At the surface 103, the conveyance means 115 may be communicatively coupled to an electronics and processing system and/or other surface equipment 160. The surface equipment 160 may include a controller having a human-machine interface (HMI) and/or other interface configured to receive commands from a human operator. The surface equipment 160 may also include a processor (or multiple internetworked processors) configured to implement one or more aspects of the methods described herein.

The downhole tool 200 may comprise a telemetry module 210, a reservoir test module 214, and a sample module 226 (among other example implementations of the component 120 depicted in in FIG. 1). Although the telemetry module 210 is shown as being implemented separate from the reservoir test module 214, the telemetry module 210 may be implemented in the reservoir test module 214. The downhole tool 200 may also comprise additional components at various locations, such as a module 208 above the telemetry module 210 and/or a module 228 below the sample module 226, which may have varying functionality within the scope of the present disclosure.

The reservoir test module 214 may comprise a selectively extendable probe assembly 216 and a selectively extendable anchoring member 218 that are respectively arranged on opposing sides of the downhole tool 200. The probe assembly 216 may be operable to selectively seal off or isolate selected portions of the sidewall of the wellbore 111. For example, the probe assembly 216 may comprise a sealing pad that may be urged against the sidewall of the wellbore 111 in a sealing manner to prevent movement of fluid into or out of the reservoir 10 other than through the probe assembly 216. The probe assembly 216 may thus be operable to fluidly couple a pump 221 and/or other components of the reservoir tester 214 to the adjacent reservoir 10. Accordingly, the reservoir tester 214 may be utilized to obtain fluid samples from the reservoir 10 by extracting fluid from the reservoir 10 using the pump 221. A fluid sample may thereafter be expelled through a port (not shown) into the wellbore 111, or the sample may be directed to one or more detachable chambers 227 disposed in the sample module 226. In turn, the detachable fluid collecting chambers 227 may receive and retain the reservoir fluid for subsequent testing at surface or a testing facility. The detachable sample chambers 227 may be certified for highway and/or other transportation. The module 208 and/or the module 228 may comprise additional sample chambers 227, which may also be detachable and/or certified for highway and/or other transportation.

The reservoir tester 214 may also be utilized to inject fluid into the reservoir 10 by, for example, pumping the fluid from one or more chambers 227 via the pump 221. Moreover, while the downhole tool 200 is depicted as comprising one pump 221, it may also comprise multiple pumps. The pump 221 and/or other pumps of the downhole tool 200 may also be or include a reversible pump operable to pump in two directions (e.g., into and out of the reservoir 10, into and out of the collecting chambers 227, etc.).

The probe assembly 216 may comprise one or more sensors 222 adjacent a port of the probe assembly 216, among other possible locations. The sensors 222 may be utilized to determine petrophysical and/or other parameters of a portion of the reservoir 10 (and/or of fluid in the reservoir 10) proximate the probe assembly 216. For example, the sensors 222 may be configured to measure or detect one or more of pressure, temperature, composition, electric resistivity, dielectric constant, magnetic resonance relaxation time, nuclear radiation, optical density (OD), fluorescence (FL), GOR, speed of sound, density, viscosity, and/or combinations thereof, although other types of sensors are also within the scope of the present disclosure.

The reservoir tester 214 may also comprise a fluid sensing unit 220 through which obtained fluid samples may flow, such as to measure properties and/or composition data of the sampled fluid. For example, the fluid sensing unit 220 may comprise one or more of a spectrometer, a fluorescence sensor, an optical fluid analyzer, a density and/or viscosity sensor, and/or a pressure and/or temperature sensor, among others.

The telemetry module 210 and/or another portion of the downhole tool 200 may comprise a downhole controller and/or control system 212 communicatively coupled to the surface equipment 160 (e.g., via the conveyance means 115). The surface equipment 160 and/or the downhole controller and/or control system 212 may be configured to control the probe assembly 216 and/or the extraction of fluid samples from the reservoir 10, such as via the pumping rate of pump 221. The surface equipment 160 and/or the downhole controller and/or control system 212 may be further configured to analyze and/or process data obtained from sensors disposed in the fluid sensing unit 220 and/or the sensors 222, store measurements or processed data, and/or communicate measurements or processed data to surface equipment or another component for subsequent analysis.

Figure 3:
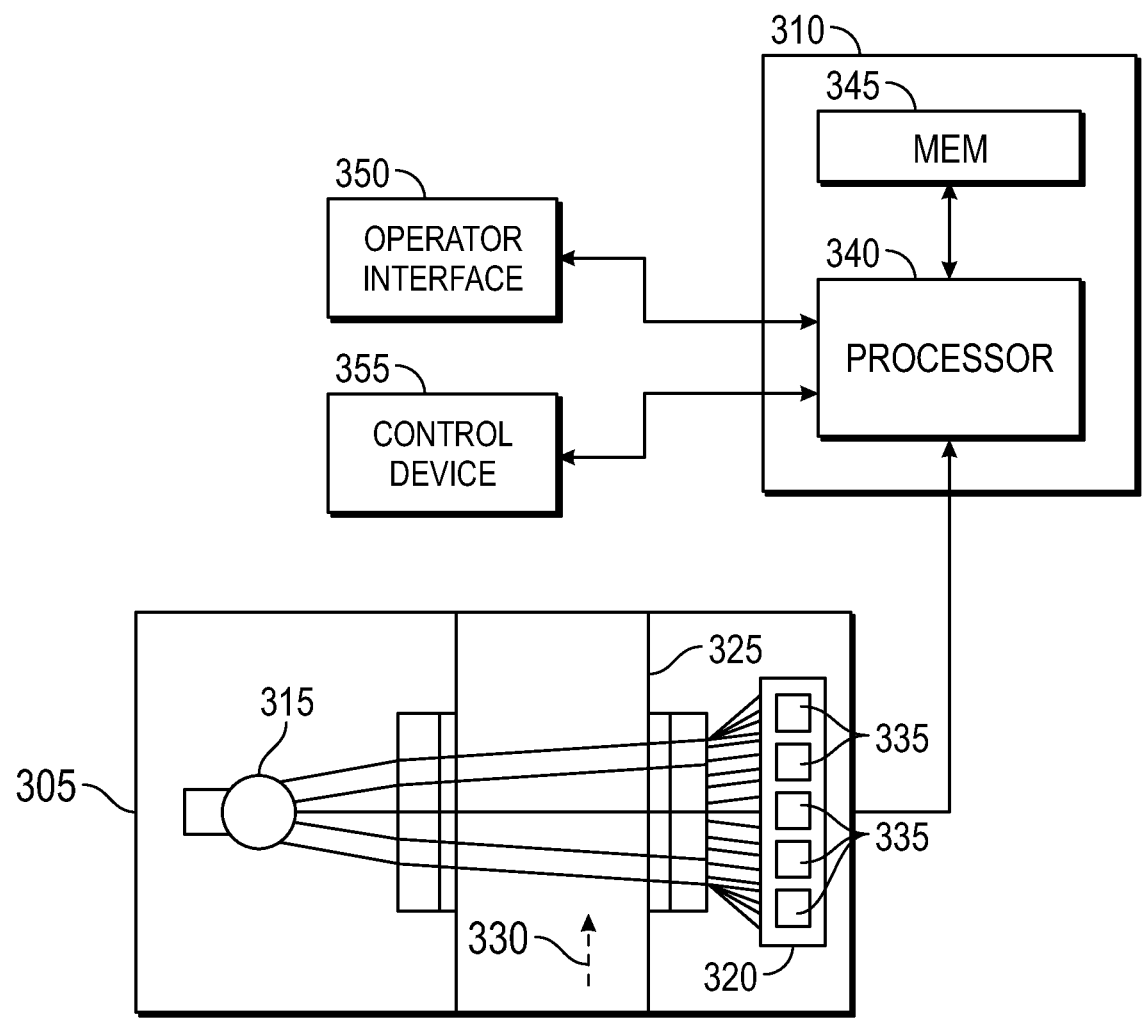
FIG. 3 is a schematic view of at least a portion of an example implementation of apparatus according to one or more aspects of the present disclosure.

FIG. 3 depicts an example implementation of a spectrometer 305 and a control/monitoring system 310 that may individually and/or collectively form a portion of the downhole tool 100 shown in FIG. 1, the downhole tool 200 shown in FIG. 2, and/or other downhole tools within the scope of the present disclosure, and that may be utilized to estimate or determine OD and/or other properties of fluid obtained from the reservoir 10. The spectrometer 305 may comprise a light source 315 and a detector 320 disposed on opposite sides of a flowline 325 through which the pumped reservoir fluid flows, as indicated by arrow 330. The spectrometer 305 may be located at various possible locations along the flowline 325. Although a single light source 315 is depicted in the example shown in FIG. 3, the spectrometer 305 may include additional light sources 315.

The detector 320 senses the light that passes through the reservoir fluid in the flowline 325. The detector 320 may include one or more detector elements 335 that may each be operable to measure the amount of light transmitted at a certain wavelength. For example, the detector elements 335 may detect the light transmitted from the visible to near-infrared within a range of 1, 5, 10, 20, or more different wavelengths ranging between about 400 nm and about 2200 nm. However, other numbers of wavelengths (corresponding to the number of detector elements) and other ranges of wavelengths are also within the scope of the present disclosure. For example, optical characteristics of the reservoir fluid may be detected at a range of wavelengths, such as the near infrared (NIR) wavelength range of approximately 800-2500 nm, 1500-2050 nm, or 1600-1800 nm. Estimations of reservoir fluid properties according to one or more aspects of the present disclosure may utilize optical data collected at a single wavelength, at multiple wavelengths, a range of wavelengths, and/or multiple ranges of wavelengths.

The spectrometer 305 may measure one or more optical characteristics of the reservoir fluid flowing through the flowline 325 and output optical spectra and/or other data representative of the detected optical characteristics. The optical characteristics may include OD of the reservoir fluid at each of the detected wavelengths and/or wavelength ranges. The OD is a logarithmic measurement relating the intensity of light emitted from the light source 315 to the intensity of light detected by the detector 320 at a certain wavelength or range of wavelengths. Each wavelength or wavelength range may correspond to a compositional component of the reservoir fluid. For example, each wavelength or wavelength range may pertain to a corresponding one of $CO_2$, $C_1$, $C_2$, $C_3$, $C_4$, $C_5$, and $C_{6+}$, although other arrangements are also within the scope of the present disclosure.

The spectrometer 305 may send optical spectra and/or other data representative of the measured optical characteristics to a processor 340 of the control/monitoring system 310. In the context of the present disclosure, the term "processor" refers to one or multiple processor components. The processor 340 may include a single processor disposed onboard the downhole tool. In other implementations, at least a portion of the processor 340 (e.g., when multiple processors collectively operate as the processor 340) may be located within the wellsite surface equipment 160. The processor 340 may also or instead be or include one or more processors located within the downhole tool and connected to one or more processors located in drilling and/or other equipment disposed at the wellsite surface 103. Moreover, various combinations of processors may be considered part of the processor 340. Similar terminology is applied with respect to the control/monitoring system 310 as well as a memory 345 of the control/monitoring system 310, meaning that the control/monitoring system 310 may include various processors communicatively coupled to each other and/or various memories at various locations.

The control/monitoring system 310 may estimate or otherwise determine one or more parameters of the reservoir fluid based on the OD data received from the spectrometer 305, a density sensor, a pressure sensor, a temperature sensor, and/or other sensors, and may utilize the parameters to determine density, OD, GOR, mass fractions of compositional components, pressure, temperature, composition, electric resistivity, dielectric constant, magnetic resonance relaxation time, nuclear radiation, FL, speed of sound, viscosity, combinations thereof, and/or other properties of the reservoir fluid. To make these and other determinations, the processor 340 may execute instructions stored in the memory 345.

The processor 340 may be communicatively coupled with one or more operator interfaces 350 and/or control devices 355. The operator interface 350 may include logs of predicted and/or measured reservoir fluid properties that are accessible to an operator. The control device 355 may include one or more devices and/or portions thereof that receive control signals for operation based on the estimated properties of the reservoir fluid. Such control devices 355 may implement changes in depth of the downhole tool within the wellbore 111, adjustments to the pumping pressure of the pump(s) of the downhole tool, and/or other control functions, perhaps based on obtained, calculated, and/or estimated reservoir fluid properties.

Figure 4:
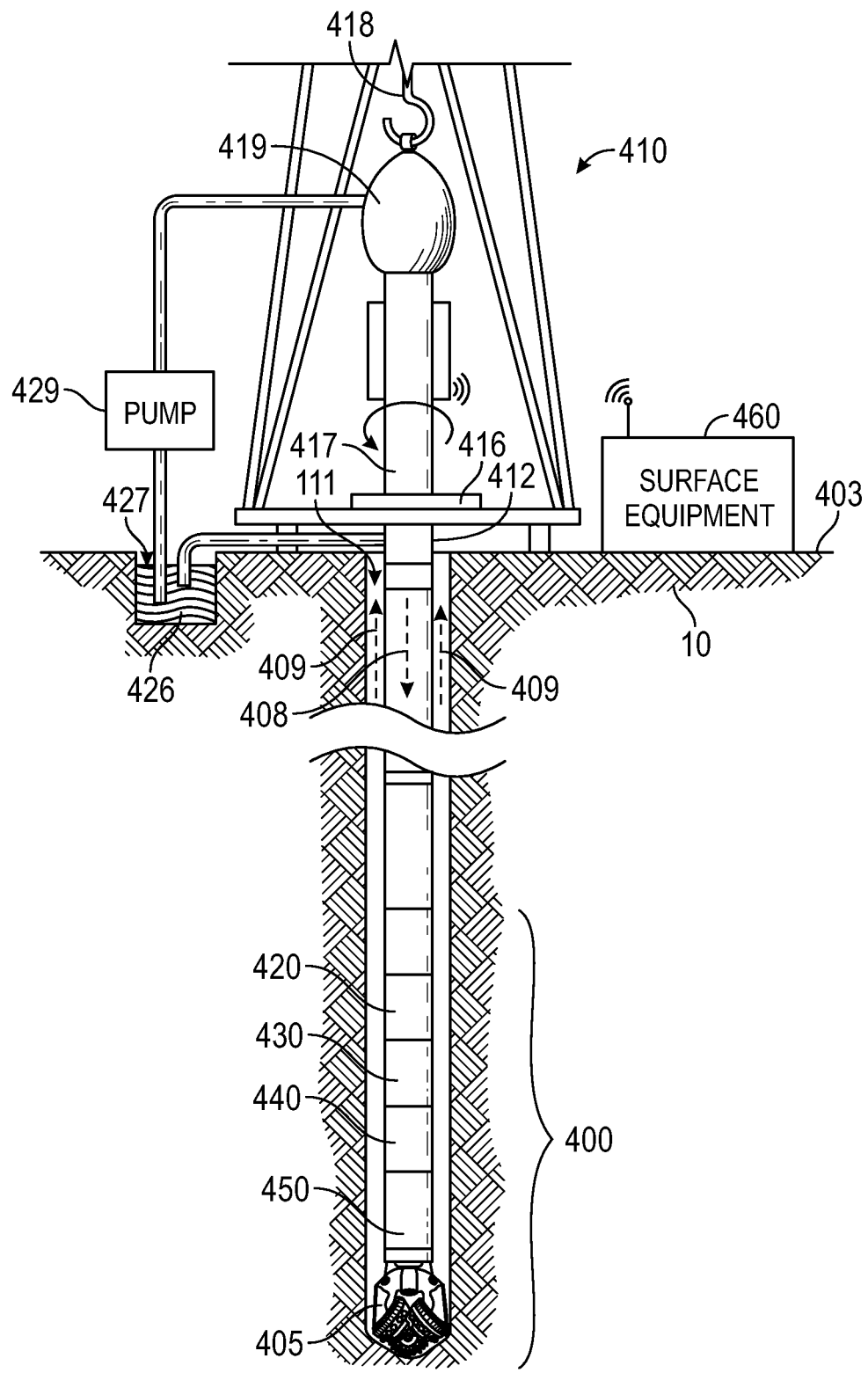
FIG. 4 is a schematic view of at least a portion of an example implementation of apparatus according to one or more aspects of the present disclosure.

FIG. 4 is a schematic view of another example wellsite system that can be employed onshore and/or offshore, perhaps including at the same wellsite as depicted in one or more of the figures described above, where the wellbore 111 may have been formed in the one or more subsurface reservoirs by rotary and/or directional drilling. FIG. 4 represents another example environment in which one or more aspects described above may be implemented, such as to perform one or more aspects of the methods within the scope of the present disclosure.

As depicted in FIG. 4, a conveyance means 412 suspended within the wellbore 111 may comprise or be connected to a bottom hole assembly (BHA) 400, which may have a drill bit 405 at its lower end. The conveyance means 412 may comprise drill pipe, wired drill pipe (WDP), tough logging conditions (TLC) pipe, coiled tubing, and/or other means of conveying the BHA 400 within the wellbore 111.

The surface system at the wellsite surface 403 may comprise a platform, rig, derrick, and/or other wellsite structure 410 positioned over the wellbore 111. The wellsite structure 410 may be substantially similar or identical to the wellsite structure shown in one or more of the figures described above. The wellsite structure 410 may include a rotary table 416, a kelly 417, a hook 418, and/or a rotary swivel 419. The conveyance means 412 may be rotated by the rotary table 416, energized by means not shown, which may engage the kelly 417 at the upper end of the conveyance means 412. The conveyance means 412 may be suspended from the hook 418, which may be attached to a traveling block (not shown), and through the kelly 417 and the rotary swivel 419, which permits rotation of the conveyance means 412 relative to the hook 418. Additionally, or instead, a top drive system may be used.

The surface system may also include drilling fluid 426, which is commonly referred to in the industry as mud, stored in a pit 427 formed at the wellsite. A pump 429 may deliver the drilling fluid 426 to the interior of the conveyance means 412 via a port (not shown) in the swivel 419, causing the drilling fluid to flow downwardly through the conveyance means 412, as indicated by directional arrow 408. The drilling fluid 426 may exit the conveyance means 412 via ports in the drill bit 405, and then circulate upward through the annulus region between the outside of the conveyance means 412 and the wall of the wellbore 111, as indicated by directional arrows 409. The drilling fluid 426 may be used to lubricate the drill bit 405 and/or carry cuttings up to the surface 403 as it is returned to the pit 427 for recirculation. Although not pictured, one or more other circulation implementations are also within the scope of the present disclosure, such as a reverse circulation implementation in which the drilling fluid 426 is pumped down the annulus region (i.e., opposite to directional arrows 409) to return to the surface 403 within the interior of the conveyance means 412 (i.e., opposite to directional arrow 408).

The BHA 400 may include various numbers and/or types of downhole tools, schematically depicted in FIG. 4 as downhole tools 420, 430, and 450. One or more of the downhole tools 420, 430, and 450 may be or comprise an acoustic tool, a density tool, a DFA tool, a directional drilling tool, a drilling tool, an EM tool, a formation evaluation tool, a gravity tool, a logging while drilling (LWD) tool, a magnetic resonance tool, a measurement while drilling (MWD) tool, a monitoring tool, a neutron tool, a nuclear tool, a photoelectric factor tool, a porosity tool, a reservoir characterization tool, a resistivity tool, a sampling tool, a seismic tool, a surveying tool, a telemetry tool, and/or a tough logging condition (TLC) tool, although other downhole tools are also within the scope of the present disclosure. One or more of the downhole tools 420, 430, and 450 may be utilized to perform at least a portion of a method according to one or more aspects of the present disclosure.

The downhole tools 420, 430, and/or 450 may be housed in a special type of drill collar, as it is known in the art, and may include capabilities for measuring, processing, and/or storing information, as well as for communicating with the other downhole tools 420, 430, and/or 450, and/or directly with a logging and control system and/or other surface equipment 460. Such communication may utilize one or more conventional and/or future-developed two-way telemetry systems, such as may be or comprise a mud-pulse telemetry system, a wired drill pipe telemetry system, an electromagnetic telemetry system, and/or an acoustic telemetry system, among others within the scope of the present disclosure. One or more of the downhole tools 420, 430, and/or 450 may also comprise an apparatus 440 for generating electrical power for use by the BHA 400. Example devices to generate electrical power include, but are not limited to, a battery system and a mud turbine generator powered by the flow of the drilling fluid.

While FIGS. 1, 2, and 4 illustrate example wellsite systems that convey a downhole tool/string into a wellbore, other example implementations within the scope of the present disclosure may utilize other conveyance means to convey a tool into a wellbore, including coiled tubing, tough logging conditions (TLC), slickline, and others. Additionally, other downhole tools comprising components in a non-modular construction are also within the scope of this disclosure.

The present disclosure introduces utilizing a downhole tool in a wellbore with a method to determine AOP and saturation point(s) (Pb or Pd) of reservoir fluids while the downhole tool is in or conveyed within the wellbore, such as while pulling (uphole) the downhole tool out of the wellbore. The downhole tool may have one or more of the aspects described above with respect to the downhole tools shown in FIGS. 1-4. An example implementation of such method is described below.

To measure fluid properties with DFA as pressure and temperature change, the following may be performed. On the last station (e.g., the furthest downhole station or the furthest uphole station), a probe, packer, and/or other fluid communication means of the downhole tool (referred to hereafter as the "probe," although merely for the sake of convenience) is engaged with the wellbore sidewall and fluid is pumped from the formation and through the fluid analyzer of the downhole tool. A sample of the fluid may also be collected in the downhole tool. The probe is then retracted while leaving the flowline exposed to hydrostatic pressure. For example, multi-sampler and/or other valves may be kept open if the DFA sensor(s) is on the downstream side of the fluid pump within the downhole tool, or probe isolation valves may be kept open if the DFA sensor(s) is on the upstream side of the pump. As another example, if the DFA sensor(s) is on the upstream side (below the pump), isolation valves in the probe may be closed to permit depressurized fluid through one or more associated check valves. In either implementation, among others within the scope of the present disclosure, the DFA sensor(s) initially in fluid communication the subterranean reservoir being tested at the current downhole station transition to being in fluid communication with fluid in the wellbore as a result of the probe retraction. A station log and a depth log are then recorded, and the downhole tool is pulled back to surface or otherwise conveyed within the wellbore with continued recording from the DFA sensor(s). From the DFA measurement(s), one can then establish saturation pressure and AOP pressure, and also establish one or more relationships between different measurements/parameters (e.g., optical density (OD), composition (e.g., C1, C2, C3-5, C6+, H2S, CO2), GOR, density, viscosity) with pressure and/or temperature change.

Fluorescence measurements may also be obtained and utilized to determine AOP and saturation points. These may have well-suited characteristics for determination of AOP and saturation points downhole. A fluid instability indicator may be determined based on fluorescence measurements downhole. Coupled with OD, GOR, and/or other measurements, this method may be utilized to more accurately determine AOP and/or saturation points of formation fluids downhole, relative to existing methods. Fluorescence measurements may also be used to determine AOP when utilizing modular sample chambers, sample bottles, or both.

Thus, methods introduced herein may entail collecting fluid within a fluid analysis system of a downhole tool, and then removing the downhole tool from the wellbore or otherwise conveying the downhole tool within the wellbore while the collected fluid is exposed to the wellbore (e.g., annulus) pressure. Measurements for the collected fluid, such as OD, GOR, fluid density, fluid viscosity, fluorescence, temperature, and pressure, among others, may be recorded continuously or at intervals as the downhole tool is conveyed within the wellbore. Corresponding measurements of the wellbore pressure also may be recorded as the downhole tool is conveyed within the wellbore, such as corresponding measurements of the decreasing wellbore pressure as the downhole tool is brought to the wellsite surface. The measurements may be employed to determine properties of the analyzed/sample formation fluid, such as the saturation pressure and the asphaltene onset pressure, among other properties.

In some implementations, the fluid pumped from the formation may be trapped in a closed system within the downhole tool, and then the trapped fluid may be compressed or decompressed in the fluid system. The closed system can be a part of flowline isolated by valves, a chamber in a bypass flowline which can be closed or opened by one or more valves, one or more of the sample bottles described above, and/or other closed configurations. After trapping the fluid in the closed system, compressing and decompressing the trapped fluid may be via the pump of the downhole tool, or a piston (e.g., driven by motor) in the sample chamber may be used to compress or decompress the trapped fluid. However, other means for compressing and decompressing the trapped fluid are also within the scope of the present disclosure. Sensors placed in the closed system acquire various measurements, such as density, pressure, temperature, viscosity, OD, and/or others.

The DFA may measure OD at different wavelengths, GOR, fluorescence intensity (FL) at different wavelengths, temperature, pressure, compositions (e.g., weight-percent (wt %) of C1, C2, C3, C4, C5, C6+, CO2), oil fraction, density, viscosity, formation volume factor (FVF), compressibility, and/or other parameters. During the DFA, as the downhole tool is pulled out of or otherwise conveyed within the wellbore, these properties are recorded and can be used as inputs for determination of AOP and saturation points.

OD at a given wavelength is the negative logarithm of the ratio of the transmitted light (I) to incident light ($I_0$), such as set forth below in Equation (1).

$$OD = -\log\left[\frac{I}{I_0}\right] = \alpha l \quad (1)$$

where l is the length of the path and a is a predetermined coefficient depending on the wavelength of I and the substance being tested. An OD of 0, 1, 2, and 3 corresponds to 100%, 10%, 1%, and 0.1% light transmission.

The DFA may measure OD, compositions, GOR, fluorescence, density, viscosity, oil fraction, FVF, compressibility, temperature, pressure, resistivity, speed of sound, and/or other parameters. These measured data may be used as inputs to determine AOP, WAT, and saturation points (Pb or/and Pd). Determining AOP and saturation points based on FL may utilize a fluorescence AOP indicator (FAI), such as set forth below in Equation (2).

$$FAI_i = \frac{FL_i(0) - FL_i(t)}{FL_i(0)} = 1 - \frac{FL_i(t)}{FL_i(0)} \quad (2)$$

where i is a specified wavelength, $FL_i$ is FL at channel i, $FL_i(0)$ is the initial FL at channel i, and $FL_i(t)$ is FL at time t and channel i.

Figure 5:
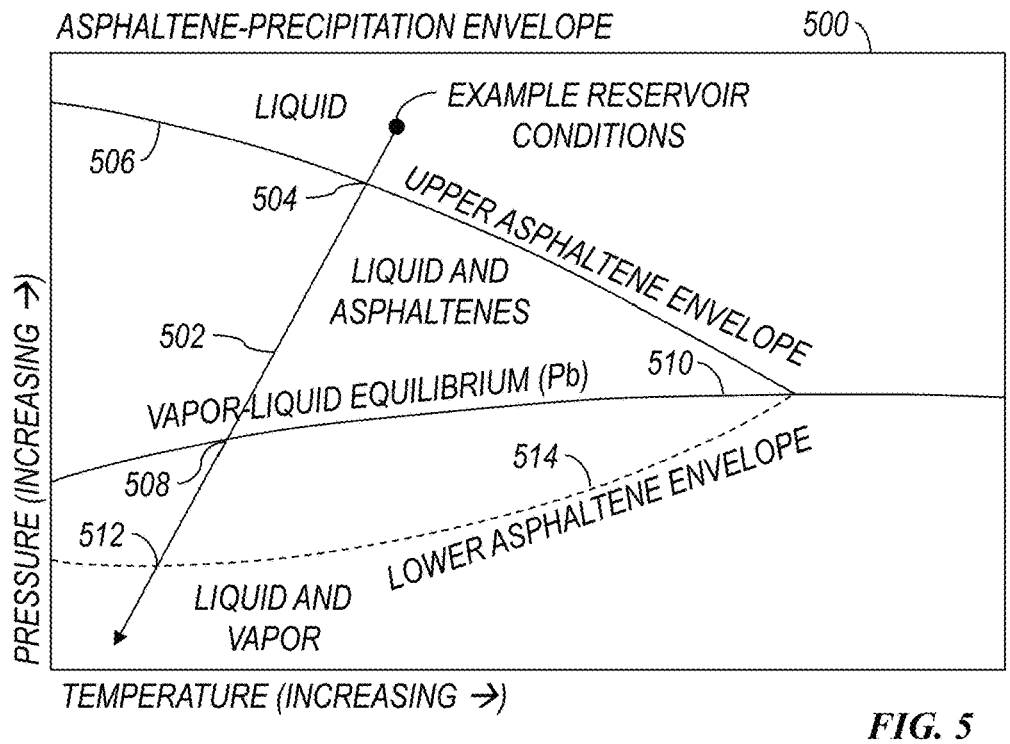
FIGS. 5-16 include graphs each depicting one or more aspects of the present disclosure.

FIG. 5 is an example pressure-temperature phase diagram 500 for a representative reservoir fluid. During the DFA tool probe retraction from the wellbore sidewall, an amount of reservoir fluid exists in the DFA module. The environmental temperature and hydrostatic pressure reduction (lower formation temperature and borehole pressure at a shallower depth) result in a decrease in temperature and pressure of the DFA, thus yielding fluid expansion or compression. If a temperature and pressure change path is as shown in the example implementation depicted in FIG. 5 (line 502), a first phase instability occurs at upper asphaltene onset points (intersection 504 between line 502 and upper asphaltene envelope 506) where asphaltenes start precipitation, a second phase instability happens at bubble points where gas bubbles start to come out of the oil (intersection 508 between line 502 and vapor-liquid equilibrium 510), and a third phase change is the lower asphaltene onset points where the precipitated asphaltenes are collectively dissolved back into oil (intersection 512 between line 502 and lower asphaltene envelope 514), such as from a thermodynamic point of view, i.e., assuming that asphaltene precipitation processes are thermodynamically reversible.

Figure 6:
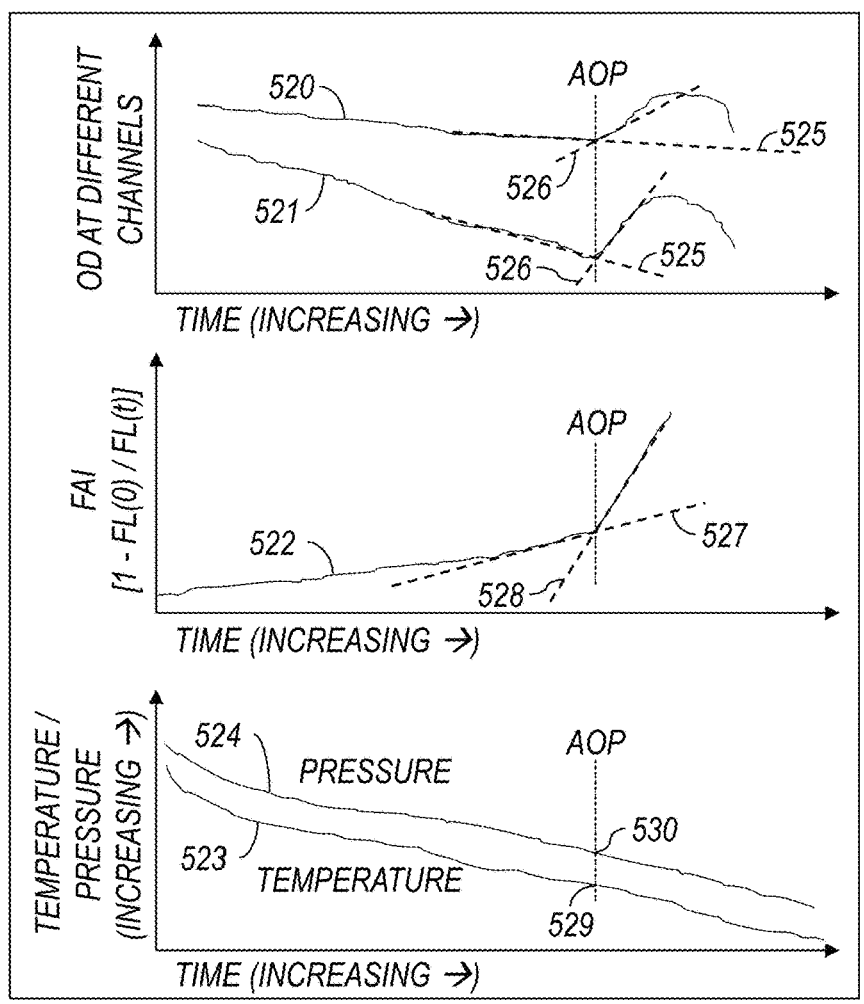

FIG. 6 depicts an example implementation of AOP determination using plots of OD (top), FAI (middle), and pressure and temperature (bottom) versus elapsed time. FIG. 6 includes a plot of OD at different channels (520, 521) with unsaturated OD values (OD<=3) versus elapsed time, a plot of FAI at different channels (522) versus elapsed time, and a plot of temperature (523) and pressure (524) versus elapsed time.

In a single oil (liquid) phase, a decrease in temperature results in fluid shrinkage, and an increase in density and OD. On the other hand, a decrease in pressure causes a reduction of density and OD. Thus, the impacts of temperature and pressure on density and OD are opposite. Therefore, OD in this region is slightly changing (either decreasing or increasing, depending on expansion or compression). Asphaltenes start to precipitate out from oil at the upper asphaltene onset point. When pressure and temperature cross the upper asphaltene onset boundary, the light transmittance falls even farther, thus yielding an increase in OD, because large clusters and floccules of asphaltenes scatter more light. OD increases much faster after AOP than those in the single oil phase (before AOP). According to these aspects, two intervals may be selected, one for the single oil phase, and the other for the two phases. A linear regression method (or other non-linear function regression methods) may then be utilized to fit OD data in the single oil phase (525) and after AOP (526). The intersection point of the two curves 525, 526 for each channel corresponds to AOP. Because flocculated asphaltene particles result in wavelength-dependent light scattering, OD data have similar behaviors at different channels, but larger light scattering in short wavelengths, as shown in the top panel of FIG. 6.

Fluorescence measurement in DFA may be an independent sensor. If AOP determined from fluorescence measurement is the same as that from OD, then more confidence is obtained for the AOP determination. Similarly to OD, FL slightly decreases or increases with elapsed time in a single oil phase. FL decreases or increases with elapsed time after AOP much faster than those in the single oil phase, depending on different situations. Therefore, FAI increases or decreases with elapsed time after AOP much faster than those in the single oil phase. If, as in the example depicted in FIG. 6, FAI 522 from two channels substantially overlap, one fluorescence channel can be used for determining AOP and saturation points. According to these aspects, two intervals (before and after AOP) can be selected. A linear regression method (or other non-linear function regression methods) may then be utilized to fit FL data in the single oil phase (527) and after AOP (528). The intersection point of the two curves 527, 528 corresponds to AOP. The top and middle panels of FIG. 6 demonstrate that the AOP from OD and the AOP from FL are consistent. The bottom panel of FIG. 6 thus indicates the AOP temperature 529 and the AOP pressure 530, utilizing the AOP determined utilizing OD and/or FAI.

Figure 7:
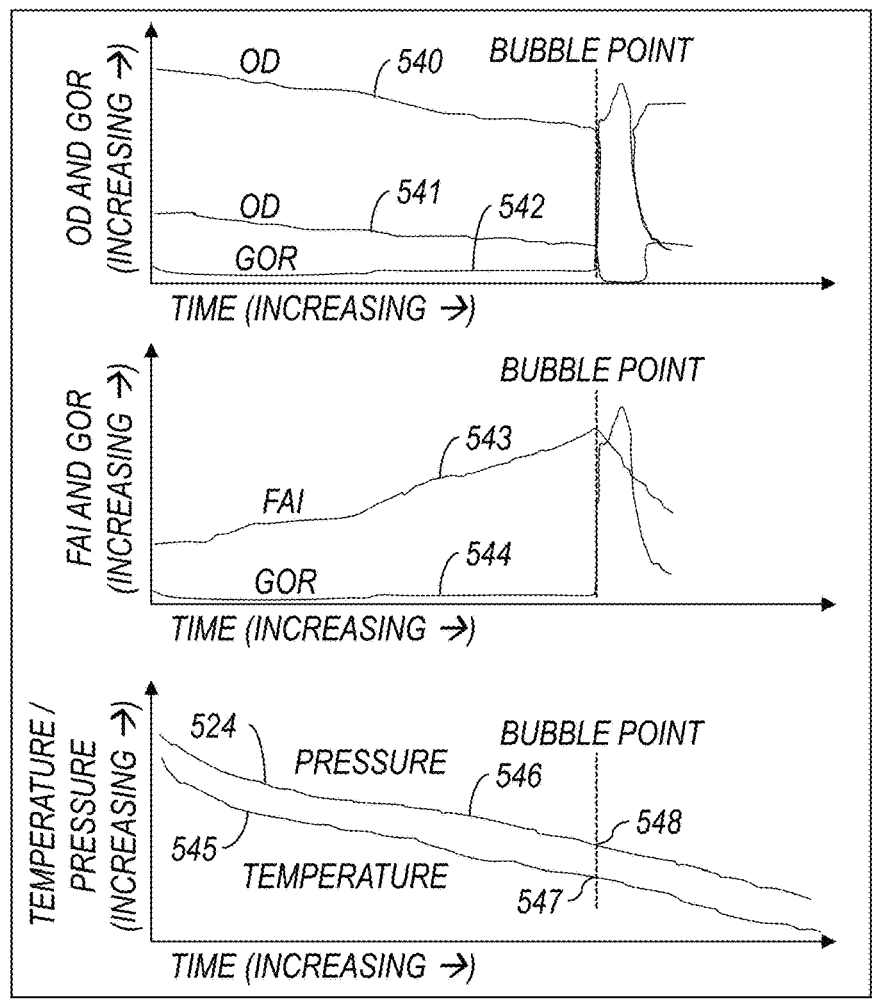

FIG. 7 depicts example representations that may be utilized in determining bubble point according to one or more aspects of the present disclosure. FIG. 7 includes a plot of OD at different channels 540, 541 with unsaturated OD values (OD<=3) and GOR 542 versus elapsed time, a plot of FAI at different channels 543 and GOR 544 versus elapsed time, and a plot of temperature 545 and pressure 546 versus elapsed time.

Light transmittance increases (OD decreases) as bubbles of gas are created at the bubble point. This response is in contrast to that of some oils, which exhibit decreased transmittance (increased OD) with the appearance of gas bubbles. Therefore, GOR may also or instead be used to verify the bubble point, because gas bubbles significantly increase GOR. Similarly, although not depicted in the top panel of FIG. 7, the bubble point may also be determined to be where C1 composition significantly increases and/or un-normalized oil fraction considerably decreases.

At the bubble point, FL reaches a minimum and FAI reaches a maximum. This response is in contrast to that of some oils, which may not be the minimum or maximum. Thus, GOR may also or instead be used to verify the bubble point, because gas bubbles significantly increase GOR. Similarly, although not depicted in the middle panel of FIG. 7, C1 composition and un-normalized oil fraction can also or instead be used for verification of the bubble point.

The top and middle panels of FIG. 7 demonstrate that the bubble points from GOR, OD, and fluorescence measurements are consistent in the depicted example. The lower panel of FIG. 7 thus depicts the bubble point temperature 547 and pressure 548, utilizing the AOP determined utilizing OD, FAI, and/or GOR.

Figure 8:
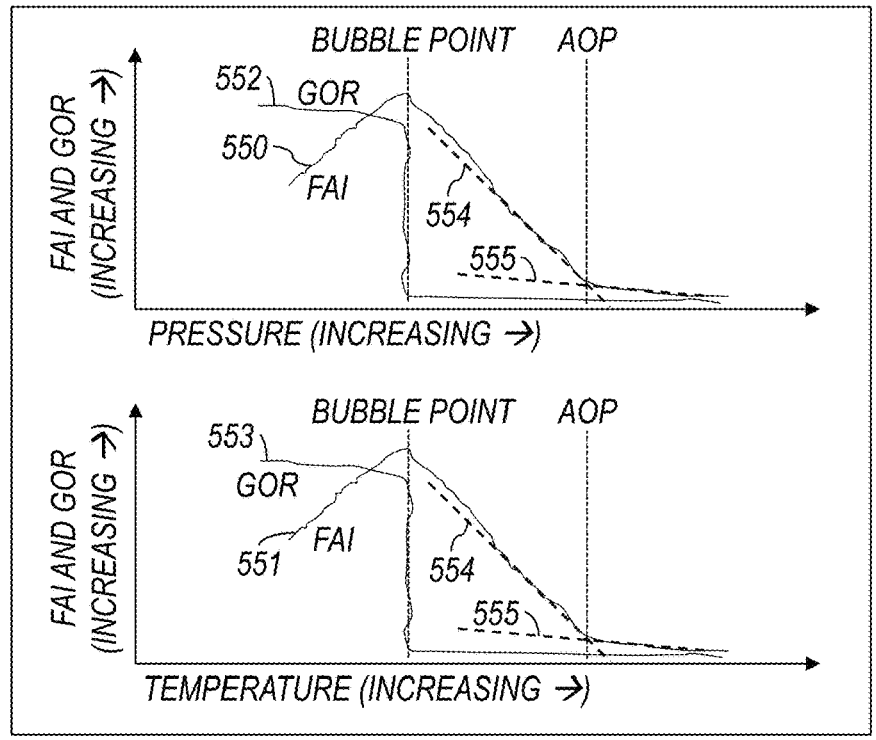

FIG. 8 depicts an example implementation in which FAI 550, 551 and GOR 552, 553 are plotted against pressure and temperature. As similarly described above, intervals for AOP (single oil phase and after AOP) may be selected, such that a linear or other regression 554 may be performed for the single oil phase interval and a linear or other regression 555 may be performed for the after AOP interval, and AOP may be determined via the intersection of the two curves 554, 555. Bubble points may be obtained by locating the maximum FAI and/or a significant GOR increase, C1 compositions increasing, and/or un-normalized oil fraction decreasing.

Figure 9:
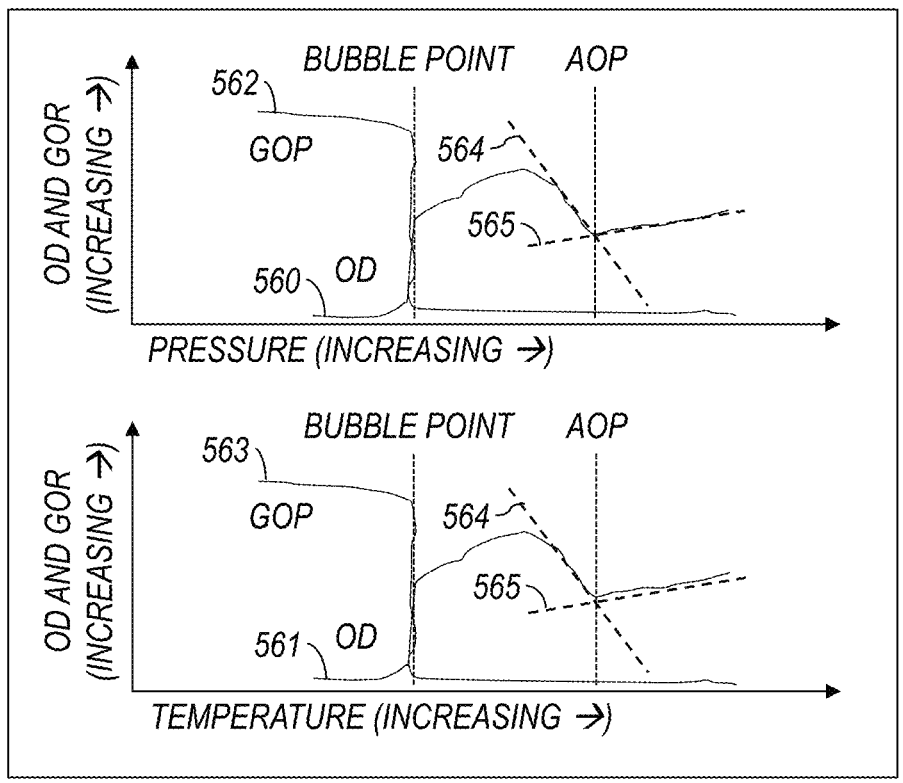

FIG. 9 similarly depicts an example implementation in which OD 560, 561 and GOR 562, 563 may be plotted against pressure and temperature. As above, intervals for AOP (single oil phase and after AOP) may be selected, such that a linear or other regression 564 may be performed for the single oil phase interval and a linear or other regression 565 may be performed for the after AOP interval, and AOP may be determined via the intersection of the two curves 564, 565. Bubble points may be obtained by locating the maximum FAI and/or a significant GOR increase, C1 compositions increasing, and/or un-normalized oil fraction decreasing.

Figure 10:
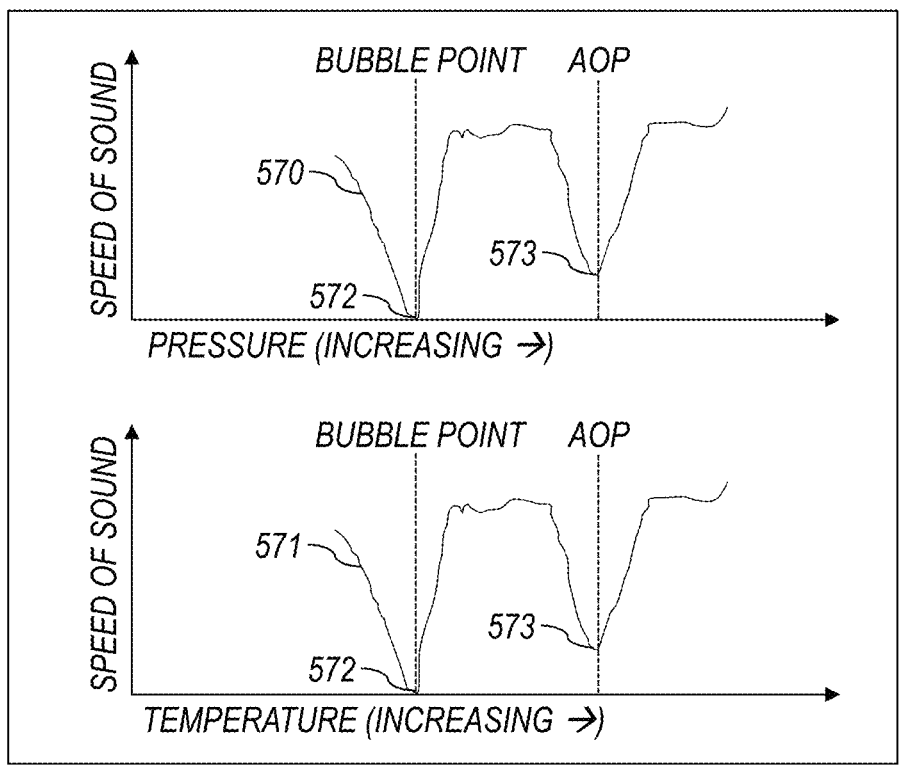

FIG. 10 depicts an example implementation in which a plot 570 of speed of sound versus pressure and a plot 571 of speed of sound versus temperature may be utilized to determine AOP and saturation points according to one or more aspects of the present disclosure. Both plots demonstrate that a first minimum 572 of speed of sound versus pressure and/or temperature may be utilized to determine bubble point, and a second minimum 573 of speed of sound versus pressure and/or temperature may be utilized to determine AOP.

DFA measurements may also be used to detect, either from one or more bulk fluid measurement properties or from one or more artifacts on the sensors, the phase change and/or other fluid property changes when the fluid is submitted to a change of pressure or temperature downhole. For example, AOP determination quality control may be performed using wavelength dependency. Optical spectrums before (pre) and after (post) AOP may be compared to show a monotonic increase with shorter wavelength, which is indicative of AOP determination accuracy. That is, a delta OD (e.g., $OD(\lambda)_{postAOP}-OD(\lambda)_{preAOP}$) may be determined and plotted versus wavelength ($\lambda$), and AOP accuracy may be assessed based on how monotonically the delta OD varies with decreasing wavelength.

Figure 11:
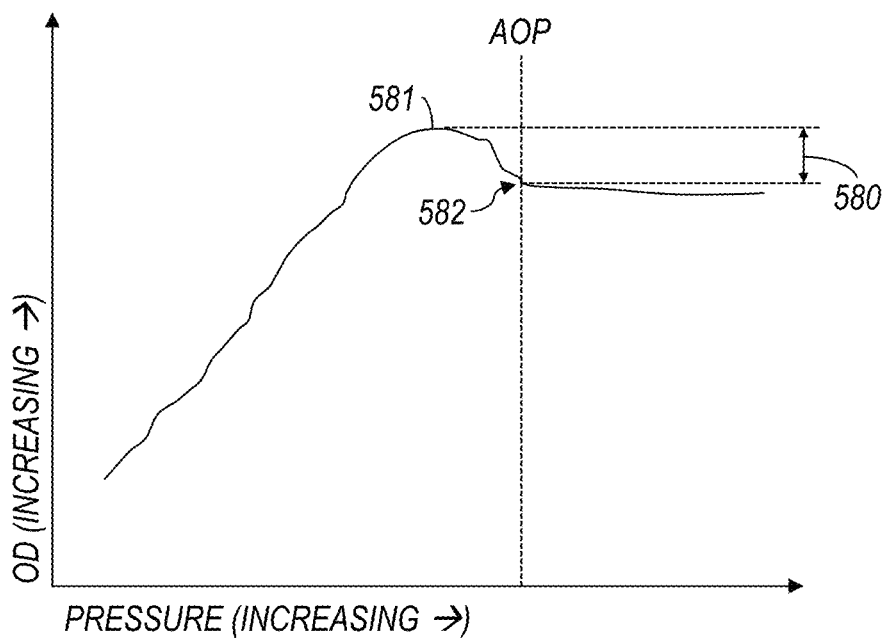
Figure 12:
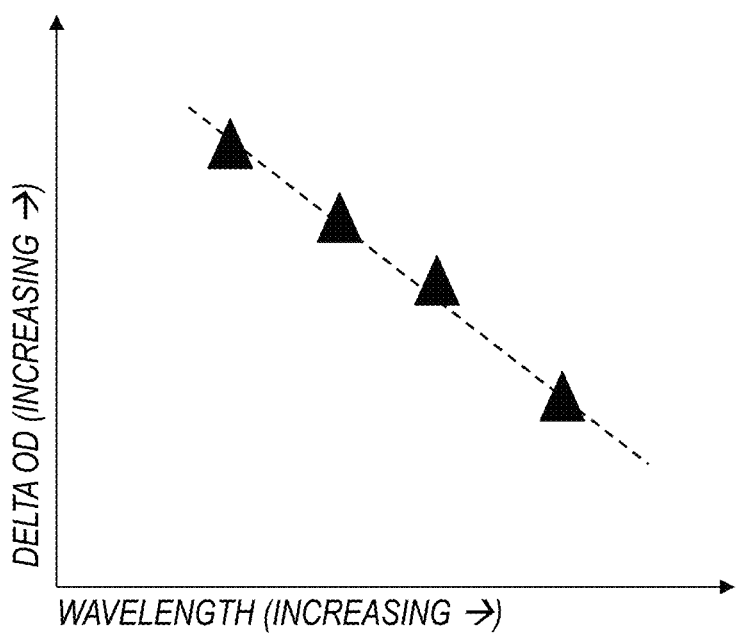

For example, FIG. 11 depicts OD relative to pressure for selected wavelength. The delta OD 580 is indicated as the difference between the peak OD (pre-AOP) 581 and the maximum OD after AOP (e.g., at AOP) 582. This delta OD approach is performed at multiple wavelengths, and then the delta OD values may be plotted versus wavelength, as depicted in FIG. 12. As shown in FIG. 12, the shorter the wavelength, the higher the delta OD, thus demonstrating a monotonic dependence on wavelength scattering. In contrast, if the delta OD did not vary substantially monotonically with decreasing wavelength, this would indicate an inaccuracy in the AOP determination.

Figure 13:
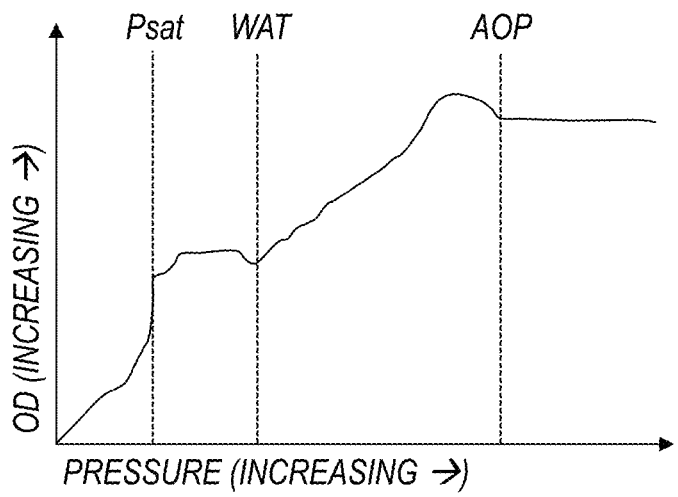
Figure 14:
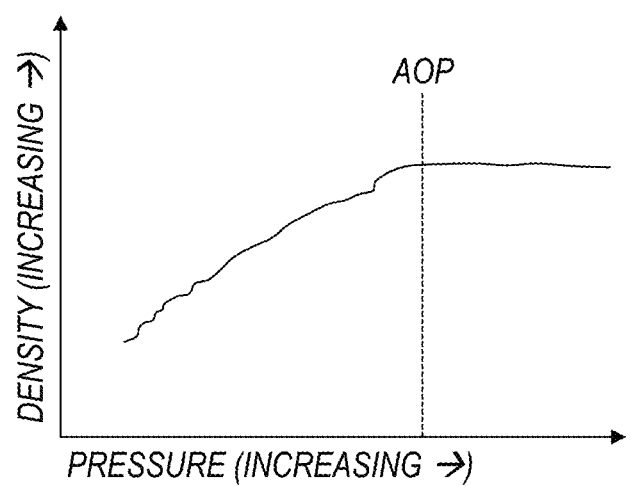
Figure 15:
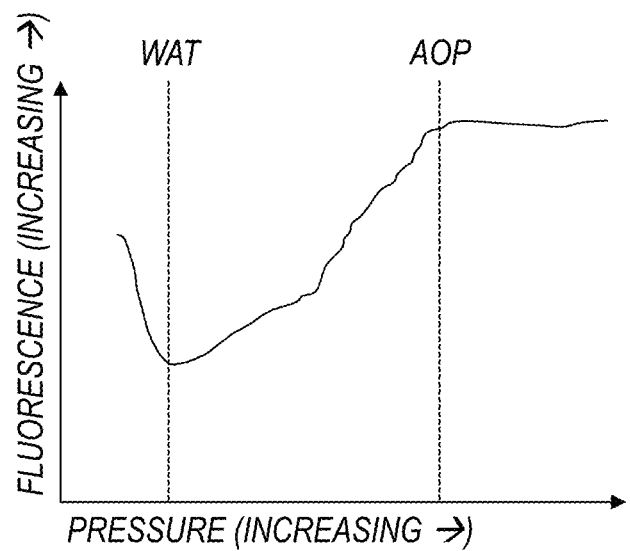
Figure 16:
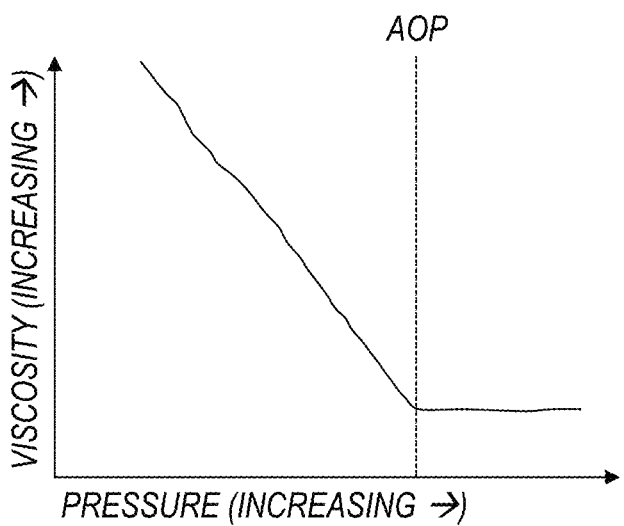

In other implementations, a change or discontinuity in data from a sensor (such as OD, density, viscosity, NMR, compressibility, FVF, speed of sound, FL, resistivity, interfacial tension, dielectric constant, refractive index, and others) being the result of AOP, WAT, or saturation pressure physical phase change may be observed from a bulk fluid property measurement or artifact in the sensor. For example, the properties may be plotted versus pressure or elapsed time, and sharp changes may indicate phase changes, such as AOP, WAT, or saturation points. Examples are depicted in FIGS. 13-16. For example, FIG. 13 depicts that, as pressure decreases, OD begins increasing at AOP but then decreases until WAT, and then decreases again until PSAT. FIG. 14 depicts that, as pressure decreases, density decreases after AOP. FIG. 15 depicts that, as pressure decreases, fluorescence decreases after AOP, and then increases at WAT. FIG. 16 depicts that, as pressure decreases, viscosity increases after AOP.

AOP quality control may also be performed using fluorescence. That is, fluorescence decreases after AOP is crossed as pressure lowers, then fluorescence increases with further pressure drop if there is an excess of asphaltene precipitation.

Asphaltene particle size may also be estimated from the optical density wavelength dependency. Asphaltene particles (aggregates) one the scale of one micrometer are wavelength dependent and first observed, and ten-micrometer scale asphaltene particles (aggregates) create scattering and are wavelength independent. This is also reflected in FIG. 11. By way of example, the asphaltene size m may be determined via Equation (3) set forth below.

$$m=[\log(OD2/OD1)/\log(\lambda 1/\lambda 2)] \quad (3)$$

where OD1 and OD2 are optical densities at different, selected wavelengths $\lambda 1$ and $\lambda 2$, respectively, each in the near-infrared spectrum.

Figure 17:
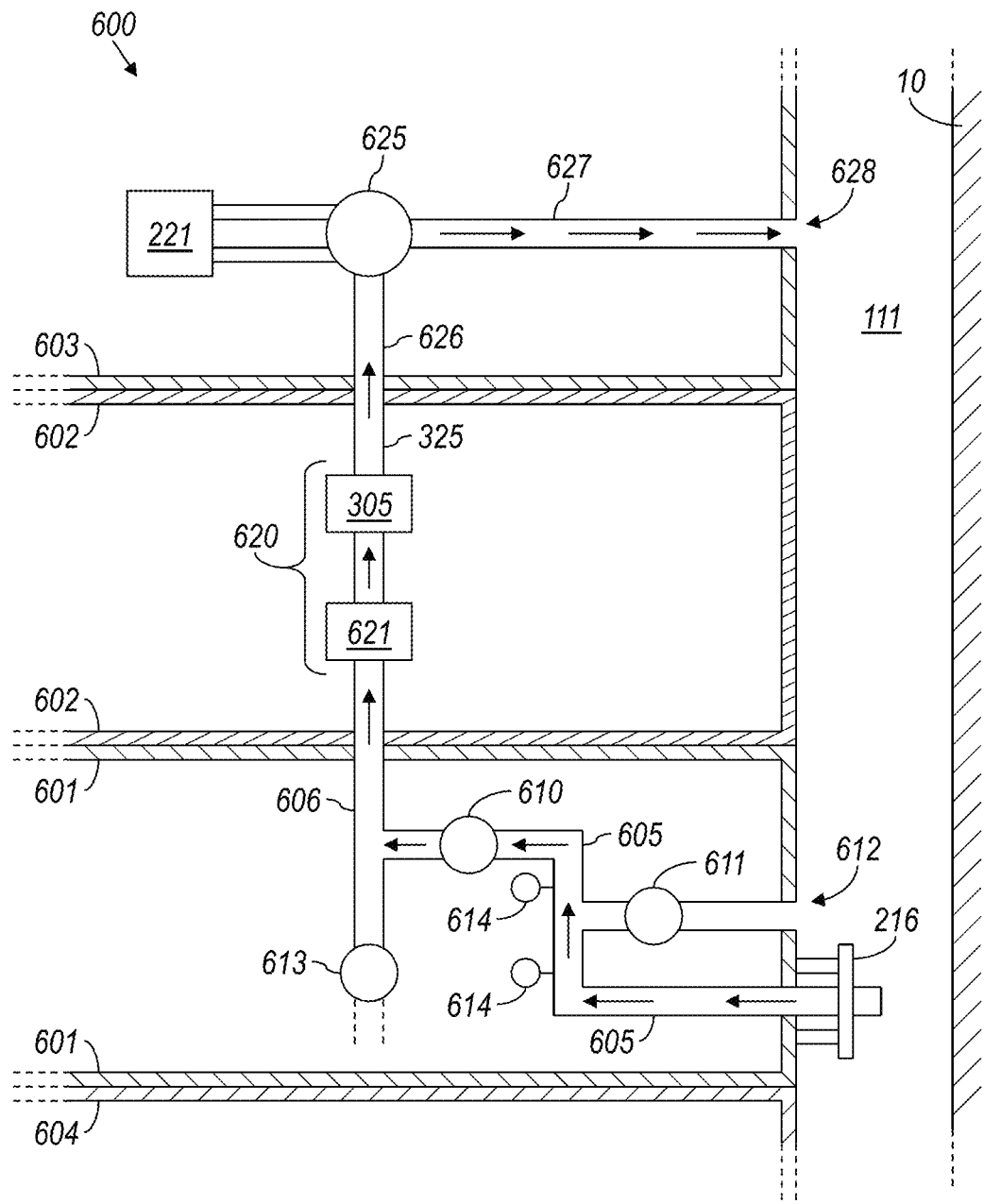
FIG. 17 is a schematic view of at least a portion of an example implementation of apparatus according to one or more aspects of the present disclosure.

FIGS. 17-20 also depict methods for determining AOP, Pb, and Pd downhole and in real-time according to one or more aspects of the present disclosure. Such methods may be the same as (or at least similar to) the methods described above. For descriptive purposes, FIG. 17 depicts another example implementation of the downhole tool 200 shown in FIG. 2, designated in FIG. 17 as downhole tool 600.

The downhole tool 600 includes a probe module 601, a DFA module 602, and a pump module 603, although other modules 604 may also exist. The probe module 601 includes a probe 216 for engaging the formation 10 such that formation fluid can be received into a flowline 605. A valve 610 may control fluid flow from the flowline 605 to another flowline 606 leading to the DFA module 602 and/or other modules 604. Another valve 611 may control fluid flow between the flowline 605 and an external port 612 exposed to the wellbore 111. Another valve 613 may control fluid flow in the flowline 606 to and/or from the DFA module 602 and/or other modules 604.

The DFA module 602 includes DFA equipment 620, such as a gas sensor 621 and the spectrometer 305, similar to as described above with respect to FIGS. 2 and 3. The flowline 325 receives fluid from the flowline 606 of the probe module 601 via suction provided by the pump 221 of the pump module 603. A valve and/or other flow control system 625 of the pump module 603 controls fluid flow amongst a flowline 626 (which receives fluid from the flowline 325), the pump 221 (or flowline(s) extending to/from the pump 221), and a flowline 627 connected with another external port 628 exposed to the wellbore 111.

The pump 221 operates to pump fluid from the formation 10 (via the probe 216), through DFA equipment 620, and back out into the wellbore 111 (via the port 628) until a target contamination level of the fluid is achieved, as determined via data from the DFA equipment 620. Then, the pump 221 may be stopped, and the fluid inside one or more portions of the downhole tool 600 (including the portion extending through the DFA equipment 620) may be pressure-isolated from the formation 10 and the wellbore 111. For example, the valves 610 and 613 and the fluid control means 625 may be operated to isolate the fluid in the flowlines 606, 325, and 626. The pump 221 (and/or another pump (not shown) of the downhole tool 600) may then be operated to lower the pressure of the trapped fluid. The DFA equipment 602 and perhaps other sensors (e.g., 614) of the downhole tool 600 are utilized to obtain measurements while the pressure drops. AOP and/or Psat (Pb and/or Pd) may then be determined utilizing the obtained measurements according to one or more aspects described above with respect to FIGS. 5-16.

Figure 18:
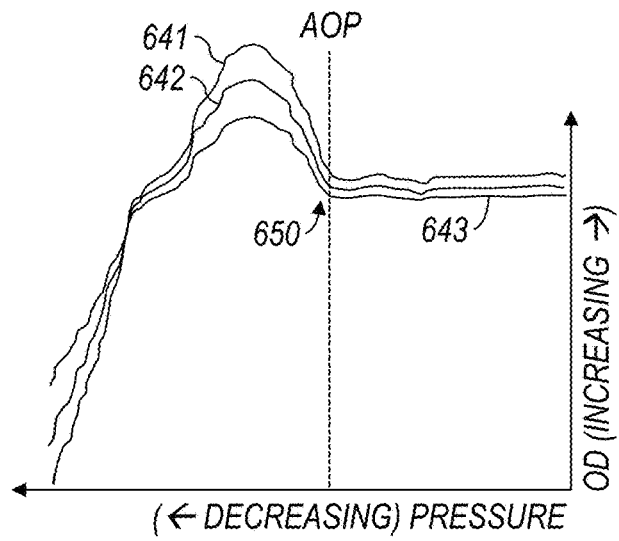
FIGS. 18-20 include graphs each depicting one or more aspects of the present disclosure.

FIG. 18 depicts an example of such operation, in which OD at different wavelengths (e.g., OD at a first wavelength 641, OD at a second wavelength 642, and OD at a third wavelength 643) are plotted against pressure. As the pressure decreases, AOP can be determined based on wavelength scattering dependency of the OD measurements, where the OD measurements begin to substantially increase 650 in value.

Figure 19:
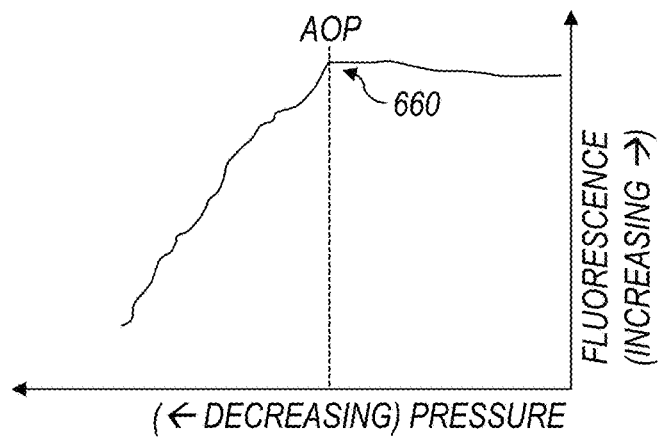

FIG. 19 depicts another example, in which FL (perhaps at different wavelengths) is plotted against pressure. As the pressure decreases, AOP can be determined based on a substantial slope change 660. FIA may similarly be utilized.

Figure 20:
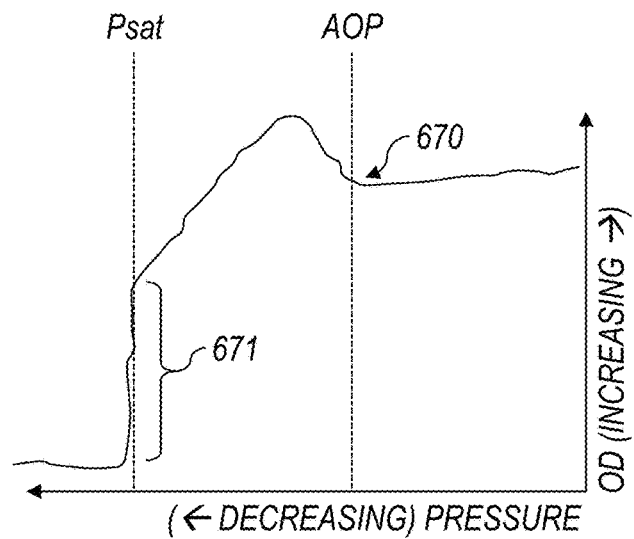

FIG. 20 depicts another example in which OD (perhaps at different wavelengths) is plotted against pressure. As the pressure decreases, AOP can be determined based on where the OD measurements begin to substantially increase 670, and Psat can be determined based on a dramatic decrease 671 in OD.

Figure 21:
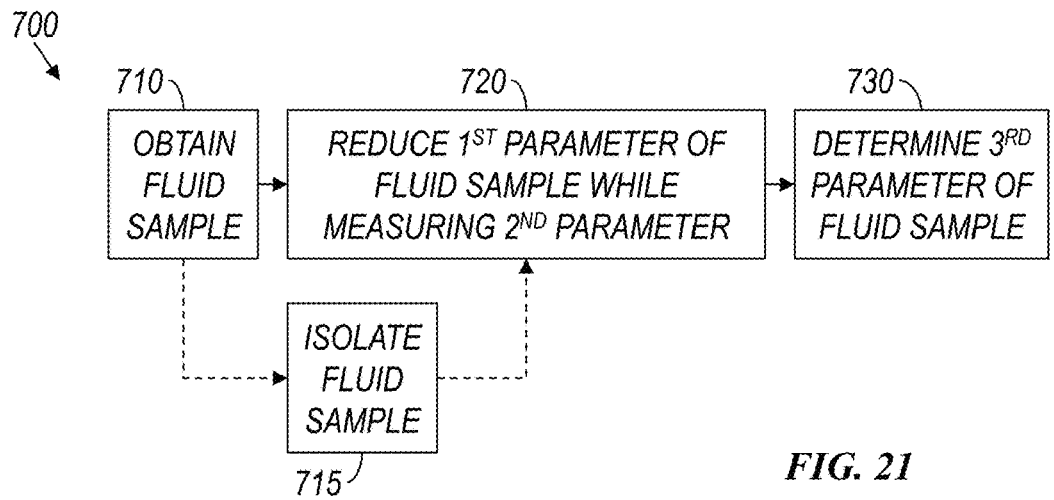
FIG. 21 is a flow-chart diagram of at least a portion of an example implementation of a method according to one or more aspects of the present disclosure.

FIG. 21 is a flow-chart diagram of at least a portion of an example implementation of a method 700 according to one or more aspects of the present disclosure. The method 700 may be, comprise, or form at least a portion of a method of determining AOP as described above, any may utilize apparatus according to one or more aspects described above, such as the downhole tools shown in one or more of FIGS. 1-4 and 17 and/or an implementation of the processing system 1000 described below and shown in FIG. 22.

The method 700 includes obtaining 710 a formation fluid sample, reducing 720 a first parameter of the obtained 710 fluid sample while measuring one or more second parameters of the obtained 710 fluid sample, and determining 730 a third parameter of the obtained 710 fluid sample utilizing the measurements.

Figure 22:
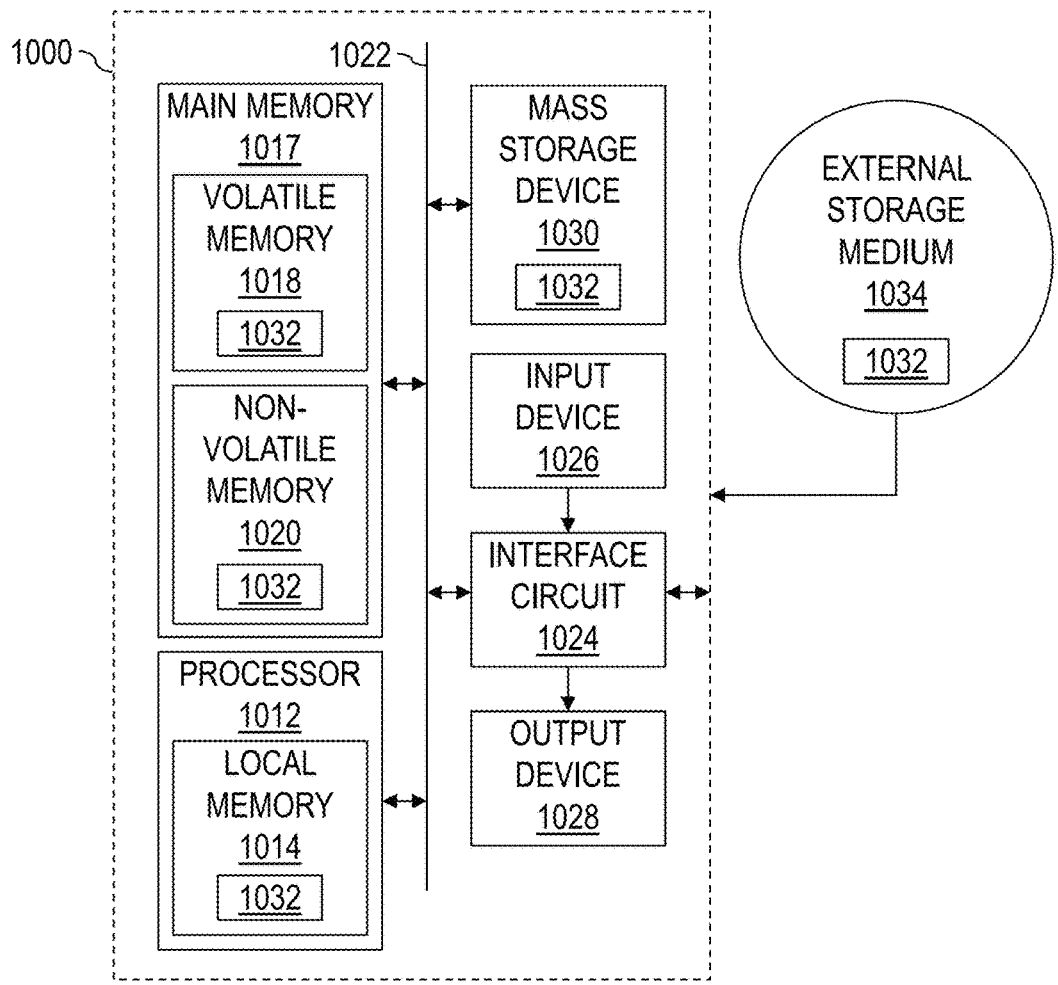
FIG. 22 is a schematic view of at least a portion of an example implementation of apparatus according to one or more aspects of the present disclosure.

Obtaining 710 the formation fluid sample may be performed via operation of a downhole tool positioned within a wellbore, such as a downhole tool having one or more aspects of the apparatus shown in one or more of FIGS. 1-4 and 17 (and perhaps FIG. 22). The reduced 720 first parameter may be pressure and/or temperature, and reducing 720 the temperature and/or pressure of the obtained 710 fluid sample may comprise conveying the downhole tool uphole within the wellbore. For example, the obtained 710 fluid sample may be in fluid communication with the wellbore, such that the uphole conveyance of the downhole tool may expose the obtained 710 fluid sample to the decreasing temperature and/or pressure of fluid within the wellbore, thereby reducing the temperature and/or pressure of the obtained 710 fluid sample.

However, the method 700 may also comprise isolating 715 the obtained 710 fluid sample within a sample chamber and/or flowline(s) of the downhole tool. In such implementations, the exposure of the downhole tool to the decreasing temperature and/or pressure of fluid within the wellbore as the downhole tool is conveyed uphole may reduce the temperature and/or pressure of the obtained 710 fluid sample even though the sample is fluidly isolated 715 within the downhole tool.

In other implementations, reducing the first parameter of the isolated 715 fluid sample may comprise operating a pump of the downhole tool to withdraw a portion of the isolated 715 fluid sample from the sample chamber and/or flowline(s), such that the first parameter may be pressure, temperature, and/or mass. Such pump operation may instead expand the volume within which the fluid sample is isolated 715, such as by moving a piston or other moveable boundary in direct or indirect fluid communication with the volume in which the fluid sample is isolated. In such implementations, the first parameter may again be pressure and/or temperature.

The measured 720 second parameters may be OD, FL, FAI, GOR, speed of sound, density, composition, and/or other properties as described above, such as in connection with one or more of FIGS. 5-16 and 18-20. Similarly, the determined 730 third parameter may be AOP, Psat, Pb, Pd, and/or WAT, as described above. The method 700 may also comprise other aspects described above, such as determining a fluid instability indicator (e.g., based on fluorescence measurements), performing quality control of AOP determination (e.g., using wavelength dependency), identifying a change or discontinuity in a sensor (e.g., being the result of AOP, WAT, and/or saturation pressure physical phase change), estimating asphaltene particle size (e.g., from optical density wavelength dependency).

FIG. 22 is a schematic view of at least a portion of an example implementation of a processing system 1000 according to one or more aspects of the present disclosure. The processing system 1000 may execute example machine-readable instructions to implement at least a portion of one or more of the methods and/or processes described herein, and/or to implement a portion of one or more of the example downhole tools described herein. The processing system 1000 may be or comprise, for example, one or more processors, controllers, special-purpose computing devices, servers, personal computers, personal digital assistant (PDA) devices, smartphones, internet appliances, and/or other types of computing devices. Moreover, while it is possible that the entirety of the processing system 1000 shown in FIG. 22 is implemented within a downhole apparatus as described above, one or more components or functions of the processing system 1000 may also or instead be implemented in wellsite surface equipment, perhaps including the surface equipment 160 depicted in FIGS. 1 and 2, the control/monitoring system 310 depicted in FIG. 3, the surface equipment 460 depicted in FIG. 4, and/or other surface equipment.

The processing system 1000 may comprise a processor 1012, such as a general-purpose programmable processor, for example. The processor 1012 may comprise a local memory 1014, and may execute program code instructions 1032 present in the local memory 1014 and/or another memory device. The processor 1012 may execute, among other things, machine-readable instructions or programs to implement the methods and/or processes described herein. The programs stored in the local memory 1014 may include program instructions or computer program code that, when executed by an associated processor, cause a controller and/or control system implemented in surface equipment and/or a downhole tool to perform tasks as described herein. The processor 1012 may be, comprise, or be implemented by one or more processors of various types operable in the local application environment, and may include one or more general-purpose processors, special-purpose processors, microprocessors, digital signal processors (DSPs), field-programmable gate arrays (FPGAs), application-specific integrated circuits (ASICs), processors based on a multi-core processor architecture, and/or other processors.

The processor 1012 may be in communication with a main memory 1017, such as via a bus 1022 and/or other communication means. The main memory 1017 may comprise a volatile memory 1018 and a non-volatile memory 1020. The volatile memory 1018 may be, comprise, or be implemented by random-access memory (RAM), static random-access memory (SRAM), synchronous dynamic random-access memory (SDRAM), dynamic random-access memory (DRAM), RAMBUS dynamic random-access memory (RDRAM), and/or other types of random-access memory devices. The non-volatile memory 1020 may be, comprise, or be implemented by read-only memory, flash memory, and/or other types of memory devices. One or more memory controllers (not shown) may control access to the volatile memory 1018 and/or the non-volatile memory 1020.

The processing system 1000 may also comprise an interface circuit 1024. The interface circuit 1024 may be, comprise, or be implemented by various types of standard interfaces, such as an Ethernet interface, a universal serial bus (USB), a third-generation input/output (3GIO) interface, a wireless interface, and/or a cellular interface, among other examples. The interface circuit 1024 may also comprise a graphics driver card. The interface circuit 1024 may also comprise a communication device, such as a modem or network interface card, to facilitate exchange of data with external computing devices via a network, such as via Ethernet connection, digital subscriber line (DSL), telephone line, coaxial cable, cellular telephone system, and/or satellite, among other examples.

One or more input devices 1026 may be connected to the interface circuit 1024. One or more of the input devices 1026 may permit a user to enter data and/or commands for utilization by the processor 1012. Each input device 1026 may be, comprise, or be implemented by a keyboard, a mouse, a touchscreen, a track-pad, a trackball, an image/code scanner, and/or a voice recognition system, among other examples.

One or more output devices 1028 may also be connected to the interface circuit 1024. One or more of the output devices 1028 may be, comprise, or be implemented by a display device, such as a liquid crystal display (LCD), a light-emitting diode (LED) display, and/or a cathode ray tube (CRT) display, among other examples. One or more of the output devices 1028 may also or instead be, comprise, or be implemented by a printer, speaker, and/or other examples.

The processing system 1000 may also comprise a mass storage device 1030 for storing machine-readable instructions and data. The mass storage device 1030 may be connected to the interface circuit 1024, such as via the bus 1022. The mass storage device 1030 may be or comprise a floppy disk drive, a hard disk drive, a compact disk (CD) drive, and/or digital versatile disk (DVD) drive, among other examples. The program code instructions 1032 may be stored in the mass storage device 1030, the volatile memory 1018, the non-volatile memory 1020, the local memory 1014, and/or on a removable storage medium 1034, such as a CD or DVD.

The mass storage device 1030, the volatile memory 1018, the non-volatile memory 1020, the local memory 1014, and/or the removable storage medium 1034 may each be a tangible, non-transitory storage medium. The modules and/or other components of the processing system 1000 may be implemented in accordance with hardware (such as in one or more integrated circuit chips, such as an ASIC), or may be implemented as software or firmware for execution by a processor. In the case of firmware or software, the implementation can be provided as a computer program product including a computer readable medium or storage structure containing computer program code (i.e., software or firmware) for execution by the processor.

In view of the entirety of the present disclosure, including the figures and the claims, a person having ordinary skill in the art will readily recognize that the present disclosure introduces a method comprising: obtaining a sample of fluid from a subterranean formation; then reducing a first parameter of the sample while measuring a second parameter of the sample, wherein the first parameter is pressure or temperature; and determining asphaltene onset point of the sample based on the second parameter measurements.

Obtaining the sample may comprise drawing the sample into a portion of a downhole tool positioned within a wellbore extending into the subterranean formation, the downhole tool portion may be at least a portion of a flowline and/or a sample chamber of the downhole tool, and reducing the first parameter may comprise conveying the downhole tool uphole within the wellbore while the downhole tool portion remains in fluid communication with the wellbore.

Obtaining the sample may comprise drawing the sample into a portion of a downhole tool positioned within a wellbore extending into the subterranean formation, and the method may further comprise, before reducing the first parameter, fluidly isolating the sample within a flowline and/or a sample chamber of the downhole tool. Reducing the first parameter may comprise conveying the downhole tool uphole within the wellbore, thereby exposing the downhole tool to wellbore fluid of decreasing temperature and/or pressure within the wellbore. Reducing the first parameter may comprise operating a pump of the downhole tool to withdraw some of the isolated sample.

The second parameter may be optical density of the sample, fluorescence intensity of the sample, speed of sound within the sample, density of the sample, or composition of the sample, among other examples.

The present disclosure also introduces a method comprising operating a downhole tool within in a wellbore that extends into a subterranean formation, wherein operating the downhole tool comprises: (A) simultaneously: (1) causing a change in a first parameter of fluid drawn into the downhole tool from the formation; and (2) determining a change in a second parameter of the fluid relative to the change in the first parameter; and (B) determining a third parameter of the fluid based on the first and second parameter changes.

Causing the change in the first parameter of the fluid may be one of: causing the fluid to decrease in pressure; causing the fluid to decrease in temperature; or causing the fluid to decrease in pressure and temperature.

Causing the change in the first parameter of the fluid may comprise exposing the fluid to the wellbore as the downhole tool is conveyed uphole within the wellbore.

Causing the change in the first parameter of the fluid may comprise conveying the downhole tool uphole within the wellbore while the fluid is fluidly isolated within the downhole tool.

Causing the change in the first parameter of the fluid may comprise operating a pump of the downhole tool. In such implementations, among others within the scope of the present disclosure, the fluid may be fluidly isolated within the downhole tool, and operating the pump may decrease the first parameter.

The third parameter may be a parameter of a change in phase of the fluid.

The phase change may be from a fluid to a fluid-solid mixture. In such implementations, among others within the scope of the present disclosure, the third parameter may be asphaltene onset point, asphaltene onset pressure, or wax appearance temperature.

The phase change may be from a liquid to a liquid-gas mixture. In such implementations, among others within the scope of the present disclosure, the third parameter may be saturation pressure or bubble point.

The phase change may be from a gas to a gas-liquid mixture. In such implementations, among others within the scope of the present disclosure, the third parameter may be saturation pressure or dew point.

The second parameter may be optical density of the fluid, fluorescence intensity of the fluid, gas/oil ratio of the fluid, speed of sound within the fluid, density of the fluid, or composition of the fluid. The second parameter may also or instead be an asphaltene onset indicator based on fluorescence of the fluid. For example, the second parameter may be an asphaltene onset indicator based on: fluorescence of the fluid prior to causing the change in the first parameter; and fluorescence of the fluid after causing the change in the first parameter.

The present disclosure also introduces a method comprising assessing an accuracy of a previously determined value of a phase-change parameter of a fluid drawn into a downhole tool from a subterranean formation, wherein the accuracy assessment comprises: at each of a plurality of different wavelengths, determining a difference between a maximum measured optical density of the fluid and another measured optical density of the fluid that corresponds to the previously determined value of the phase-change parameter; and determining whether the determined differences increase monotonically relative to decreasing values of the wavelengths.

The phase-change parameter may be pressure.

The phase-change may be asphaltene onset.

The present disclosure also introduces a computer program product comprising a non-transitory, computer-readable medium comprising instructions that, when executed by a processor of a processing system, cause the processing system to operate a downhole tool within in a wellbore that extends into a subterranean formation, wherein operating the downhole tool comprises: (A) simultaneously: (1) causing a change in a first parameter of fluid drawn into the downhole tool from the formation; and (2) determining a change in a second parameter of the fluid relative to the change in the first parameter; and (B) determining a third parameter of the fluid based on the first and second parameter changes.

The present disclosure also includes an apparatus comprising a processing system comprising a processor and a memory comprising instructions that, when executed by the processor, cause the processing system to operate in conjunction with a downhole tool within in a wellbore that extends into a subterranean formation, including to: (A) simultaneously: (1) cause a change in a first parameter of fluid drawn into the downhole tool from the formation; and (2) determine a change in a second parameter of the fluid relative to the change in the first parameter; and (B) determine a third parameter of the fluid based on the first and second parameter changes.

The present disclosure hereby incorporates herein the entirety of each of the following: U.S. Patent Application Publication No. 2017/0175524, filed Dec. 18, 2015, and titled "Systems and Methods for In-Situ Measurements of Mixed Formation Fluids;" U.S. Patent Application Publication No. 2017/0284197, filed Mar. 31, 2016, and titled "Methods for In-Situ Multi-Temperature Measurements Using Downhole Acquisition Tool;" and U.S. Pat. No. 9,303,510, issued Apr. 5, 2016, and titled "Downhole Fluid Analysis Methods."

The foregoing outlines features of example implementations so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the implementations introduced herein. A person having ordinary skill in the art should also realize that such equivalent constructions do not depart from the spirit and scope of the present disclosure, and that they may make various changes, substitutions, and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method comprising:
   obtaining a sample of fluid from a subterranean formation with a downhole tool by drawing the fluid into a portion of the downhole tool positioned within a wellbore extending into the subterranean formation;
   measuring a first parameter of the sample;
   fluidly isolating the sample within a flowline and/or a sample chamber of the downhole tool such that the fluidly isolated sample is isolated from a pressure within the wellbore and is isolated from a pressure within the subterranean formation;
   reducing the measured first parameter of the fluidly isolated sample while measuring a second parameter of the fluidly isolated sample, wherein the measured first parameter is pressure or temperature, and wherein reducing the first parameter comprises operating a pump of the downhole tool to withdraw some of the isolated sample from the flowline and/or the sample chamber while a remainder of the sample remains fluidly isolated, expanding a volume of the flowline and/or the sample chamber while the sample remains fluidly isolated, or conveying the downhole tool upwardly in the wellbore while the sample remains fluidly isolated;
   providing in real time the measured first parameter and the measured second parameter to a control/monitoring system at least partially located in the downhole tool; and
   determining asphaltene onset point of the fluidly isolated sample based on the measured second parameter, wherein the determining is done using the control/monitoring system while the tool is downhole.

2. The method of claim 1 wherein the sample is drawn into the portion of the downhole tool until a target contamination level of the fluid is achieved.

3. The method of claim 1 wherein the measured second parameter is a speed of sound within the isolated sample.

4. The method of claim 1 further comprising determining a wax appearance temperature of the sample based on the measured second parameter, wherein determining the wax appearance temperature is done using the control/monitoring system while the tool is downhole.

5. The method of claim 1 further comprising determining a wax appearance temperature of the sample based on the measured second parameter, wherein:
   determining the wax appearance temperature is done using the control/monitoring system while the tool is downhole,
   the sample is drawn into the portion of the downhole tool until a target contamination level of the fluid is achieved, and
   the measured second parameter is a speed of sound within the isolated sample.

6. The method of claim 1 wherein reducing the first parameter comprises expanding a volume of the flowline and/or the sample chamber.

7. The method of claim 6 wherein the volume is expanded by moving a piston in direct or indirect fluid communication with the volume of the flowline and/or the sample chamber.

8. The method of claim 1 wherein reducing the first parameter comprises conveying the downhole tool upwardly in the wellbore while the sample remains fluidly isolated.

9. The method of claim 1 wherein the measured first parameter is pressure, the method further comprising compressing the fluidly isolated sample prior to reducing the measured first parameter.

10. The method of claim 1 wherein the second parameter comprises a plurality of optical density (OD) measurements taken at a plurality of wavelengths ($\lambda$) both before the determined asphaltene onset point (pre-AOP) of the fluidly isolated sample and after the determined asphaltene onset point (post-AOP) of the fluidly isolated sample, the method further comprising:
   determining a delta OD according to $OD(\lambda)_{post\text{-}AOP} - OD(\lambda)_{pre\text{-}AOP}$ at each wavelength; and
   determining if the delta OD monotonically increases as the wavelength decreases.

11. The method of claim 10 further comprising assessing an accuracy of the asphaltene onset point of the sample based on how monotonically the delta OD increases as the wavelength decreases.

12. The method of claim 1 wherein the second parameter comprises a plurality of optical density (OD) measurements taken at a plurality of wavelengths (λ), the method further comprising determining an asphaltene particle size (m) according to the equation: $m=[\log(OD_2/OD_1)/\log(\lambda_1/\lambda_2)]$, wherein $OD_1$ and $OD_2$ are optical densities at different wavelengths $\lambda_1$ and $\lambda_2$, respectively, and wherein each wavelength is in the near-infrared spectrum.

13. A method comprising:
 operating a downhole tool within a wellbore that extends into a subterranean formation, wherein operating the downhole tool comprises:
 measuring a first parameter of a sample of fluid drawn into the downhole tool from the formation;
 fluidly isolating the sample within a flowline and/or a sample chamber of the downhole tool such that the fluidly isolated sample is isolated from a pressure within the wellbore and is isolated from a pressure within the subterranean formation;
 simultaneously:
  causing a change in the measured first parameter of the fluidly isolated sample of fluid, wherein causing the change in the first parameter of the sample of fluid is one of: causing the sample of fluid to decrease in pressure; causing the sample of fluid to decrease in temperature; or causing the sample of fluid to decrease in pressure and temperature, and wherein causing the change in the first parameter of the sample of fluid comprises operating a pump of the downhole tool to withdraw some of the isolated sample of fluid from the flowline and/or the sample chamber while a remainder of the sample of fluid remains fluidly isolated, expanding a volume of the flowline and/or the sample chamber while the sample of fluid remains fluidly isolated, or conveying the downhole tool upwardly in the wellbore while the sample of fluid remains fluidly isolated; and
  determining a change in a second parameter of the fluidly isolated sample of fluid relative to the change in the first parameter;
 providing in real time the measured first parameter and the determined change in the second parameter to a control/monitoring system at least partially located in the downhole tool; and
 determining a third parameter of the fluidly isolated sample of fluid based on the first and second parameter changes, wherein the determining is done using the control monitoring system while the tool is downhole.

14. The method of claim 13 wherein the fluid is drawn into the downhole tool until a target contamination level of the fluid is achieved.

15. The method of claim 13 wherein the second parameter is a speed of sound within the fluidly isolated sample of fluid, and wherein the third parameter is a wax appearance temperature.

16. The method of claim 13 wherein the third parameter is a wax appearance temperature.

17. The method of claim 13 wherein:
 the fluid is drawn into the downhole tool until a target contamination level of the fluid is achieved,
 the second parameter is a speed of sound within the fluidly isolated sample of fluid, and
 the third parameter is a wax appearance temperature.

18. The method of claim 13 wherein reducing the first parameter comprises expanding a volume of the flowline and/or the sample chamber.

19. The method of claim 13 wherein reducing the first parameter comprises conveying the downhole tool upwardly in the wellbore while the sample remains fluidly isolated.

20. The method of claim 13 wherein the third parameter is an asphaltene onset point (AOP) of the fluidly isolated sample of fluid, wherein the second parameter comprises a plurality of optical density (OD) measurements taken at a plurality of wavelengths (λ) both before the determined asphaltene onset point (pre-AOP) of the fluidly isolated sample fluid and after the determined asphaltene onset point (post-AOP) of the fluidly isolated sample of fluid, the method further comprising:
 determining a delta OD according to $OD(\lambda)_{post\text{-}AOP} - OD(\lambda)_{pre\text{-}AOP}$ at each wavelength; and
 determining if the delta OD monotonically increases as the wavelength decreases.

* * * * *